(12) United States Patent  (10) Patent No.: US 7,494,489 B2
Roh  (45) Date of Patent: Feb. 24, 2009

(54) SYSTEMS AND METHODS THAT FACILITATE MINIMALLY INVASIVE SPINE SURGERY

(75) Inventor: Jeffrey S. Roh, 400 E. 71st St., Apt. 6H, New York, NY (US) 10021

(73) Assignee: Jeffrey S. Roh, Sammamish, WA (US)

( * ) Notice: Subject to any disclaimer, the term of this patent is extended or adjusted under 35 U.S.C. 154(b) by 358 days.

(21) Appl. No.: 11/122,514

(22) Filed: May 5, 2005

(65) Prior Publication Data
US 2005/0251139 A1 Nov. 10, 2005

Related U.S. Application Data

(60) Provisional application No. 60/568,907, filed on May 7, 2004.

(51) Int. Cl.
*A61F 5/00* (2006.01)
*A61B 17/70* (2006.01)
(52) U.S. Cl. .................... 606/86 A; 606/273
(58) Field of Classification Search .............. 606/60, 606/61, 71, 72, 99, 100, 104, 86, 86 A, 266, 606/279, 273; 600/210, 201, 214, 215, 233, 600/217; 403/107, 232.1
See application file for complete search history.

(56) References Cited

U.S. PATENT DOCUMENTS

| | | | | |
|---|---|---|---|---|
| 3,054,398 | A | * | 9/1962 | Kobler .................. 600/206 |
| 5,429,121 | A | * | 7/1995 | Gadelius .................. 600/217 |
| 5,810,841 | A | | 9/1998 | McNeirney et al. |
| 5,885,292 | A | | 3/1999 | Moskovitz et al. |
| 6,096,049 | A | | 8/2000 | McNeirney et al. |
| 6,379,356 | B1 | | 4/2002 | Jackson |
| 6,440,133 | B1 | * | 8/2002 | Beale et al. .................. 606/61 |
| 6,546,277 | B1 | | 4/2003 | Franck et al. |
| 6,575,979 | B1 | | 6/2003 | Cragg |
| 6,648,888 | B1 | | 11/2003 | Shluzas |

(Continued)

FOREIGN PATENT DOCUMENTS

WO  WO2005/009303  * 2/2005  .................. 600/210

OTHER PUBLICATIONS

International Search Report dated May 6, 2005 and mailed Jun. 28, 2006 for PCT Application Serial No. PCT/US05/16236, 7 pages.

*Primary Examiner*—Pedro Philogene
(74) *Attorney, Agent, or Firm*—Amin, Turocy & Calvin, LLP

(57) ABSTRACT

A system and method that facilitates minimally invasive spine surgery. The system includes screw preparation instruments that include a targeted guide with a laser attached to a fluoroscope, at least one polyaxial screw and rod guidance instruments that selectively insert the at least one polyaxial screw within the spine. The screw preparation instruments include an awl, a hand-held drill or tap, a ball-tipped probe, a cannulated depth gauge ruler, and a hexagonal screwdriver. Each screw preparation instrument have respective handles marked with a targeting guide oriented along respective central axes of the instruments. The rod guidance instruments include a rod with a tapered tip, a T-handle rod holder, a T-handle alignment guide, an alignment marker sleeve, a flexible alignment marker with a polyaxial head, and a template rod.

19 Claims, 45 Drawing Sheets

U.S. PATENT DOCUMENTS

| | | |
|---|---|---|
| 6,783,528 B2 | 8/2004 | Prestigiacomo |
| 6,945,933 B2 * | 9/2005 | Branch et al. ............... 600/210 |
| 7,052,497 B2 | 5/2006 | Sherman et al. |
| 7,160,300 B2 * | 1/2007 | Jackson ...................... 606/61 |
| 2002/0091390 A1 | 7/2002 | Michelson |
| 2003/0176772 A1 * | 9/2003 | Yang ......................... 600/220 |
| 2005/0203517 A1 * | 9/2005 | Jahng et al. .................. 606/61 |
| 2005/0228380 A1 | 10/2005 | Moore et al. |
| 2006/0036241 A1 | 2/2006 | Siegal |

* cited by examiner

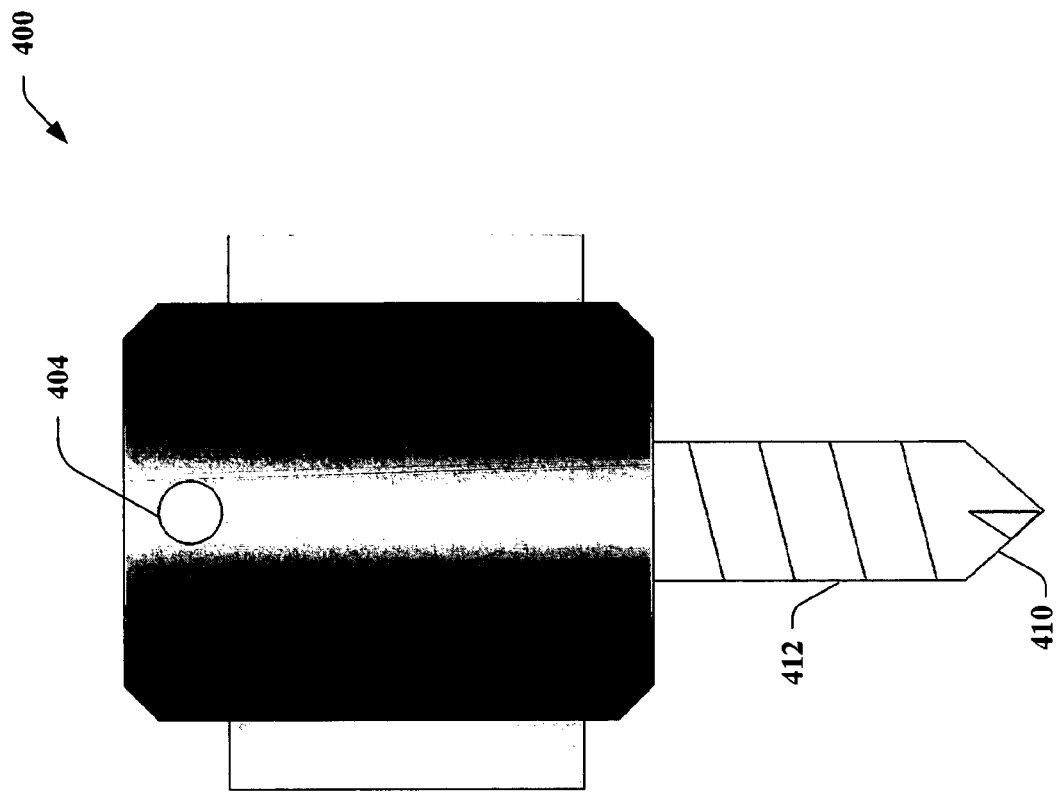
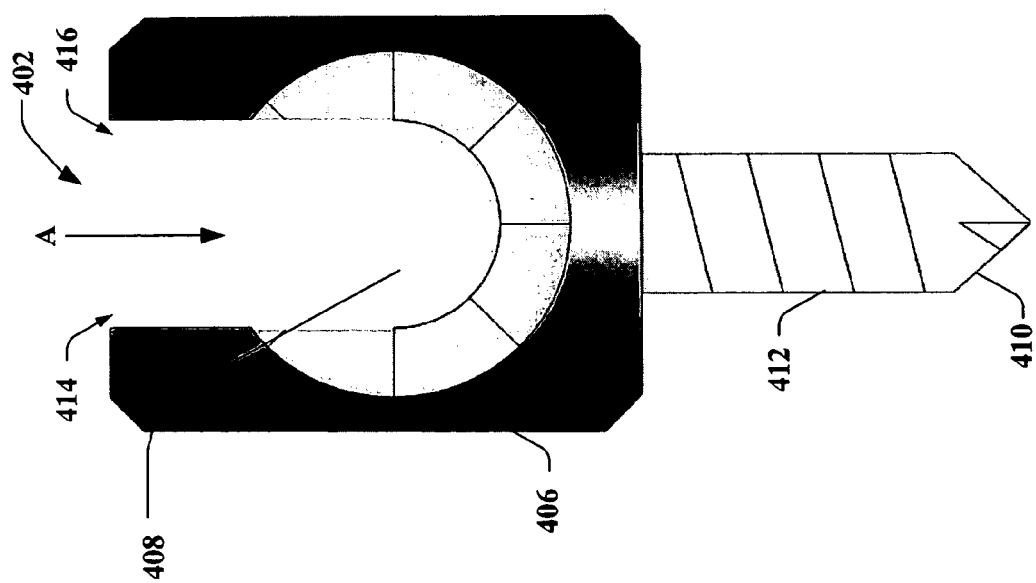
FIG. 13

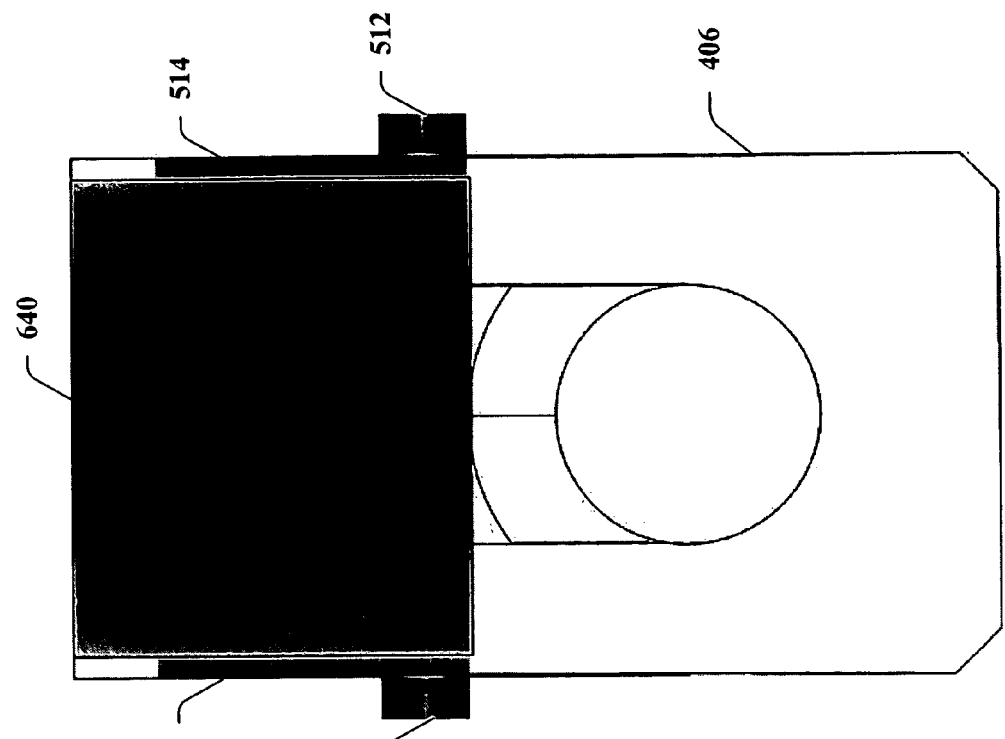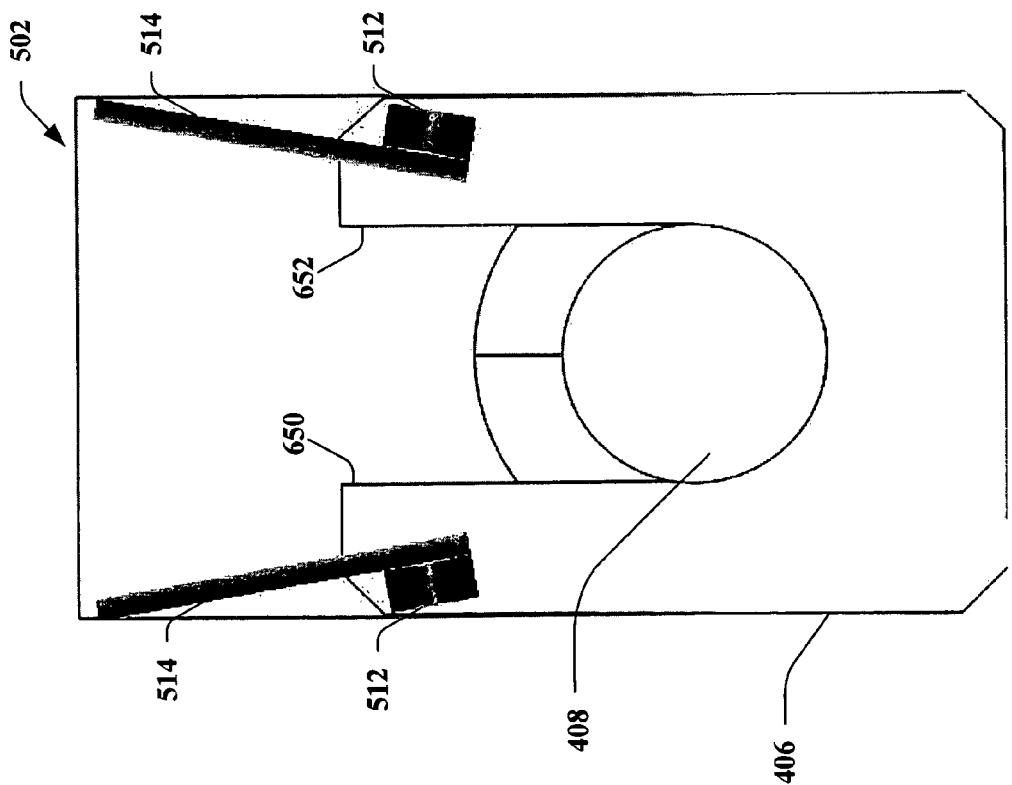
FIG. 20

SYSTEMS AND METHODS THAT FACILITATE MINIMALLY INVASIVE SPINE SURGERY

CROSS-REFERENCE TO RELATED APPLICATIONS

This application claims the benefit of U.S. Provisional Application Ser. No. 60/568,907, filed May 7, 2004, entitled "SYSTEMS AND METHODS THAT FACILITATE MINIMALLY INVASIVE SPINE SURGERY," the entirety of which is incorporated herein by reference.

TECHNICAL FIELD

This invention is related to systems and methods that facilitate spinal surgery and more particularly to facilitate minimally invasive spine surgery.

BACKGROUND OF THE INVENTION

Conventional spine surgery procedures are typically invasive and can result in considerable soft tissue trauma, discomfort, and prolonged recovery. The spine is a column of vertebrae that enclose and protect the spinal cord and neural elements. The spinal column consists of thirty-three vertebrae divided into five anatomic areas. There are seven vertebrae in the cervical spine, twelve vertebrae in the thoracic spine, five vertebrae in the lumbar spine, five fused vertebrae in the sacral spine and four vertebrae that make up the coccyx.

Non-surgical modalities such as rest and/or physical therapy are often utilized to treat symptoms associated with spinal disorders. However, if non-surgical measures fail, surgical intervention may be indicated.

Intra-operatively, surgeons commonly utilize free-hand techniques to perform spinal surgery and to fix anchoring elements to portions of the vertebrae. Through extensive training, surgeons become familiar with the bony landmarks of the spine, and utilize this knowledge to determine the proper placement of surgical devices and starting points for anchoring elements.

However, traditional techniques may lack the accuracy and precision necessary to minimize iatrogenic injury to the patient. Accordingly, there is an unmet need in the art to mitigate such shortcomings of conventional surgical spine procedures.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Percutaneous placement of spinal instrumentation in the cervical, lumbar, thoracic and sacral spine can be performed with an intraoperative laser-guided fluoroscopic technique in accordance with the subject invention. A working axis and skin incision are determined with laser-guided fluoroscopy along the central axis of a spinal pedicle. A coaxial fluoroscopic image of the pedicle cortex along its central axis projects as a circle or oval. The laser-aiming device locates the entry point on the skin or posterior spine and confirms the proper alignment of all instruments along the working axis with the targeting handle. An awl with a radiolucent targeting handle is placed along the working axis through utilization of laser-guided fluoroscopy, and an entry point is created. A guide pin or wire is inserted through the skin incision along the working axis and a working portal is established with sequential cannulated dilators. A hinged cylinder retractor can be placed over the dilators to expose the working area. A screw path is created along the working axis by placing a drill or tap with radiolucent targeting handles along the working axis. Alternatively, a cannulated drill or tap can be placed over a guide pin or wire to prepare the screw path. Integrity of the pedicle is verified with a ball-tipped probe. A length of the screw path is measured with a pedicle ruler and a polyaxial pedicle screw with a rod-guidance entry funnel is placed along the screw path with a hexagonal screwdriver. Alternatively, a cannulated polyaxial pedicle screw can be placed over a guide pin or wire following measurement of screw length. Proper placement of the drill, probe, and screw along the working axis are confirmed with biplanar fluoroscopy in the coaxial and lateral projections of the pedicle central axis. A T-handle alignment guide is secured coaxially on the polyaxial screw heads by a locking or top-loading screw mechanism. The distal end of the T-handle alignment guide can be fitted with a rod-guidance entry funnel if a standard polyaxial pedicle screw without the guidance entry funnel is not utilized. A screw alignment marker is placed coaxially on the pedicle screws through an alignment sleeve. The polyaxial ends of the alignment markers are interlocked with a connector and removed as one unit.

The length and contour of the spinal rod is determined by the three-dimensional shape of the alignment marker tips. A tapered-tip spinal rod is measured, cut to length, and contoured to match the tips of the alignment markers to fit through the rod-guidance entry funnel of the pedicle screws. The curvature of the spinal rod matches the arc through the polyaxial screw heads. The spinal rod is secured to a rod holder. A rod entry skin incision is made along the arc of rotation based on the midpoint of the first and last alignment markers. The rod is directed through the rod-guidance entry funnel of the polyaxial screw heads through bimanual control of the polyaxial screw head and rod under biplanar fluoroscopy. The rod is secured to the screw head with top loading set screws and transconnecting rod towers are aligned with their connecting rod-guidance entry funnels facing one another. The connecting rod entry point on the skin is determined with laser-guided fluoroscopic assistance. The length of the connecting rod is assessed with alignment markers and the tower set screw interlocks the connecting rod to the spinal rod by a rod-locking bolt. This instrumentation technique is utilized in conjunction with spinal arthrodesis. Anterior interbody fusion, posterior interbody fusion, transforaminal interbody fusion, or posterior spinal fusion can be performed through direct, microscopic, endoscopic, and/or fluoroscopic visualization.

To the accomplishment of the foregoing and related ends, certain illustrative aspects of the invention are described herein in connection with the following description and the annexed drawings. These aspects are indicative, however, of but a few of the various ways in which the principles of the invention can be employed and the invention is intended to include all such aspects and their equivalents. Other advantages and novel features of the invention will become apparent from the following detailed description of the invention when considered in conjunction with the drawings.

BRIEF DESCRIPTION OF THE DRAWINGS

FIGS. 13-15 illustrate an exemplary polyaxial screw according to an aspect of the invention.

FIGS. 16-24, illustrate a rod guidance system according to an aspect of the invention.

DETAILED DESCRIPTION OF THE INVENTION

Figure 1:
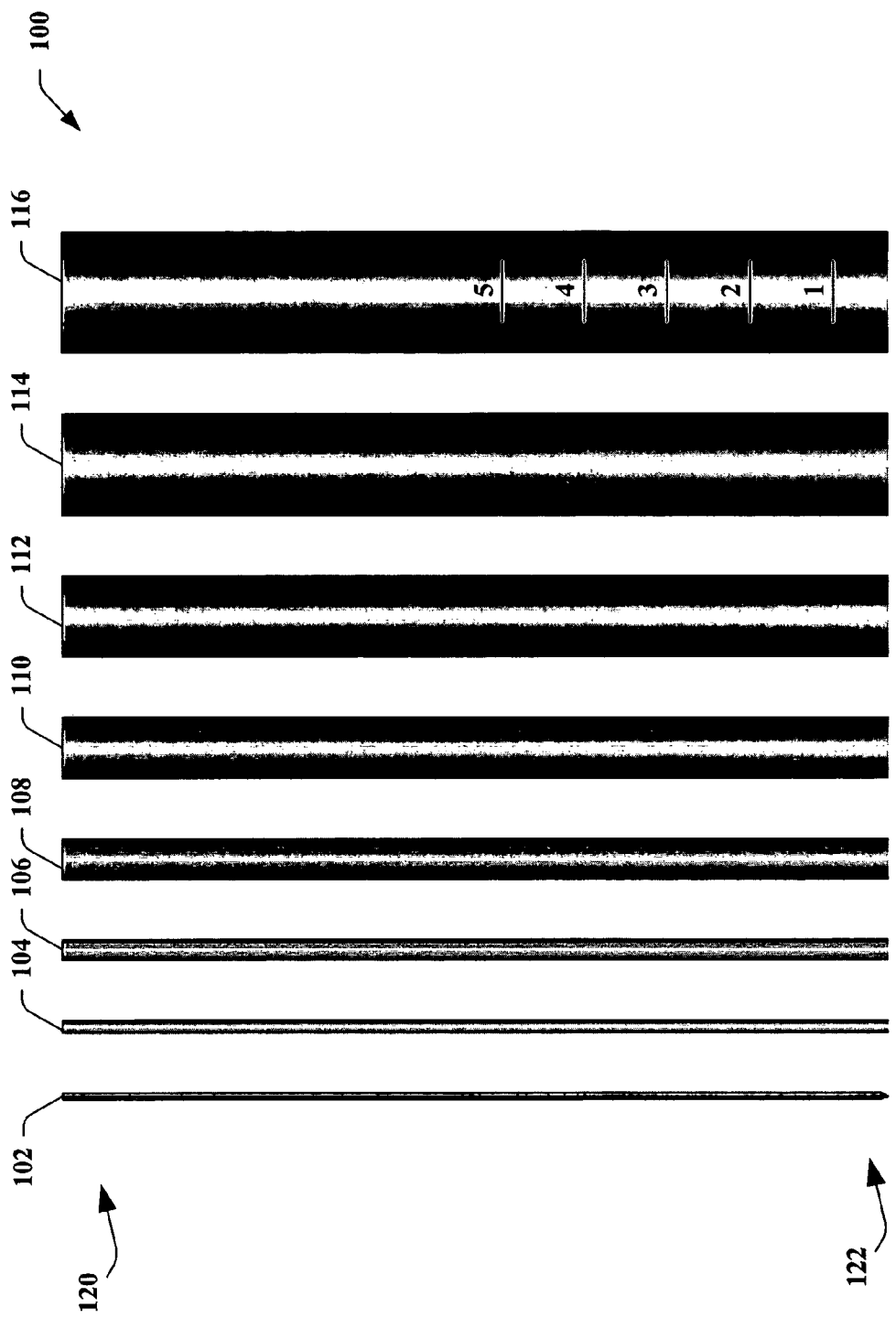
FIG. 1 illustrates a cannulated dilator system according to an aspect of the invention.

The subject invention is now described with reference to the drawings, wherein like reference numerals are used to refer to like elements throughout. In the following description, for purposes of explanation, numerous specific details are set forth in order to provide a thorough understanding of the invention. It may be evident, however, that the invention can be practiced without these specific details. In other instances, well-known structures and devices are shown in block diagram form in order to facilitate describing the invention.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured through events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring now to the figures, FIG. 1 illustrates a cannulated dilator system 100 in accordance with an aspect of the invention. A dilator is a medical instrument for dilating muscles or for stretching and/or enlarging cavities or openings. The cannulated dilator system 100 has cylindrical shaped dilators 102-116, whose diameters become sequentially larger to minimize soft tissue trauma. While eight dilators are illustrated, it will be appreciated by those skilled in the art that more than eight dilators or less than eight dilators can be utilized depending on the particular application and all such systems are intended to fall within the scope of the invention.

As illustrated, dilator 102 has a smaller diameter than dilator 104, which has a smaller diameter than dilator 106, and so forth. Each dilator 102-116 is open at both its proximal end 120 and its distal end 122. The cross-sectional shape of the dilators 102-116 is circular and the thickness of both the inner and outer diameters is uniform except at the distal end 122 where the dilator is tapered to allow for safe and easy passage through soft tissues. The outer surface of the dilators 102-116 is marked with a ruler or other marking guide, such as the exemplary markings 1-5 on dilator 116, to allow for depth assessment of the soft tissues. This measurement determines the length of a hinged cylinder retractor, which will be discussed in more detail with reference to FIG. 2 below.

The inner diameter of the smallest dilator 102 can accommodate a guide wire or pin, for example. In such a way, a pin or guide wire can be inserted down the center of the dilator 102, thus acting as a guide. In an alternate embodiment, the inner diameter of the smallest dilator 102 can be cannulated whereby a pin can be put through the dilator 102 to act as both an anchor and a guide.

Figure 2:
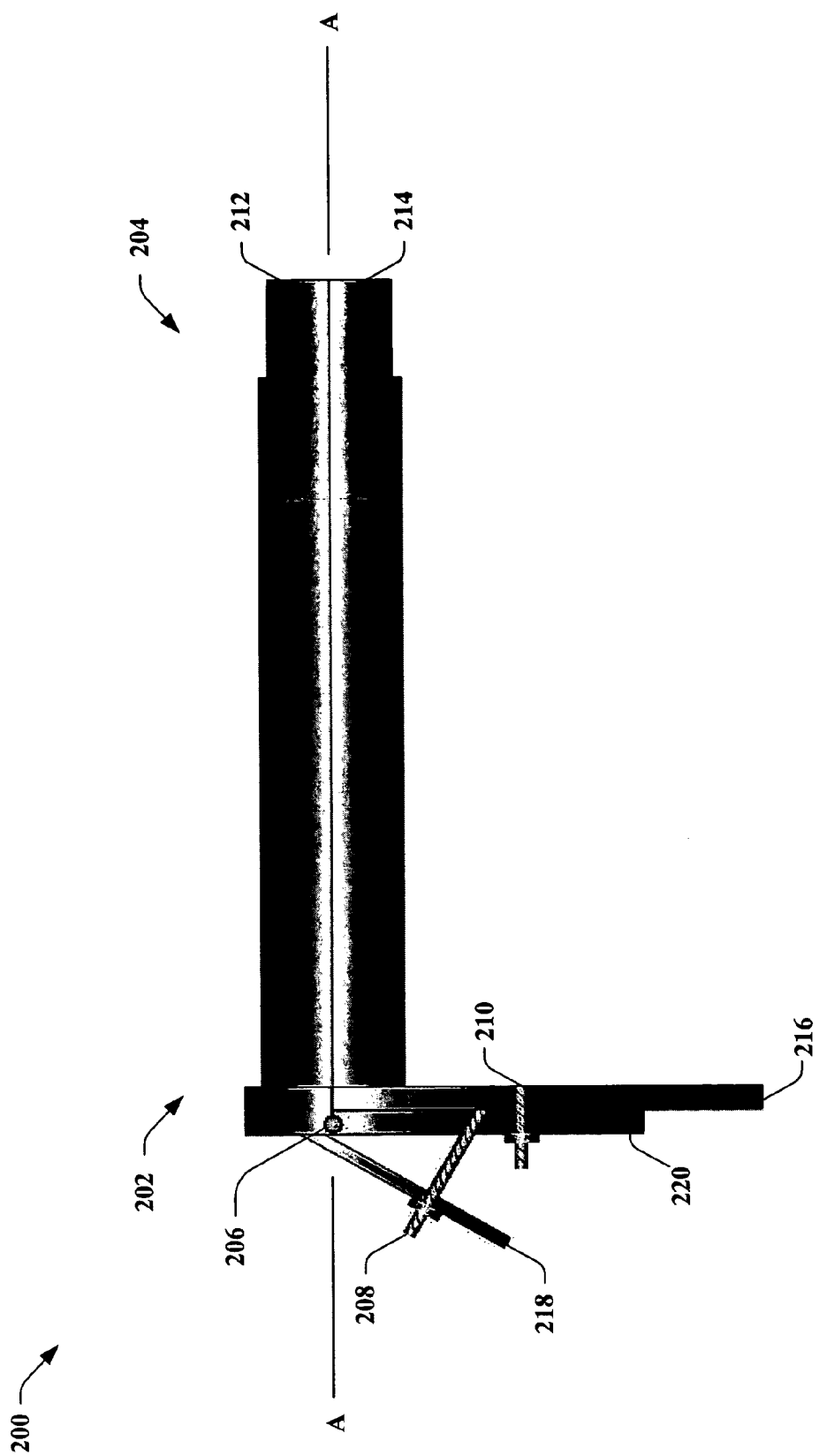
FIGS. 2-6 illustrate exemplary hinged cylinder retractors according to an aspect of the invention.

Referring now to FIGS. 2-6, illustrated is an exemplary hinged cylinder retractor 200 according to an aspect of the invention. Referring initially to FIG. 2, the hinged cylinder retractor 200 is open at both a proximal end 202 and a distal end 204. The cross-sectional shape of the cylinder 200 is round and the thicknesses of the inner and outer diameters are uniform except at the distal end 204. The distal ends 204 of the retractor 200 are tapered and may contain entry slots for utilization during spinal rod insertion. The inner diameter of the cylinder retractor 200 can accommodate the cannulated dilator system 100 illustrated in FIG. 1. The retractor 200 can be variable lengths to accommodate variable soft tissue depths.

The lower cylinder 214 has a handle 216 at its proximal end 202 that is oriented 90 degrees relative to the long axis, A, of the cylinder 200. The upper cylinder 212 has a handle 218 at its proximal end 202 that is oriented less than 90 degrees to allow for angled expansion. The upper cylinder 212 has a hinged U-shaped handle 220 located adjacent to and behind the lower cylinder handle to allow for symmetric expansion and is shown in an alternate view in FIG. 6.

Two hinges 206 are located at the proximal end 202 of the retractor 200 providing for expansion of a field of vision by allowing expansion of the two hemi-cylinders 212 and 214. The hinges 206 provide a pivot point upon which the proximal end 202 of the upper hemi-cylinder 212 pivots. In FIG. 2 the two hemi-cylinders 212 and 214 are shown in a closed position where the cylinders 212 are close together and can be touching, providing a minimal field of vision.

Figure 3:
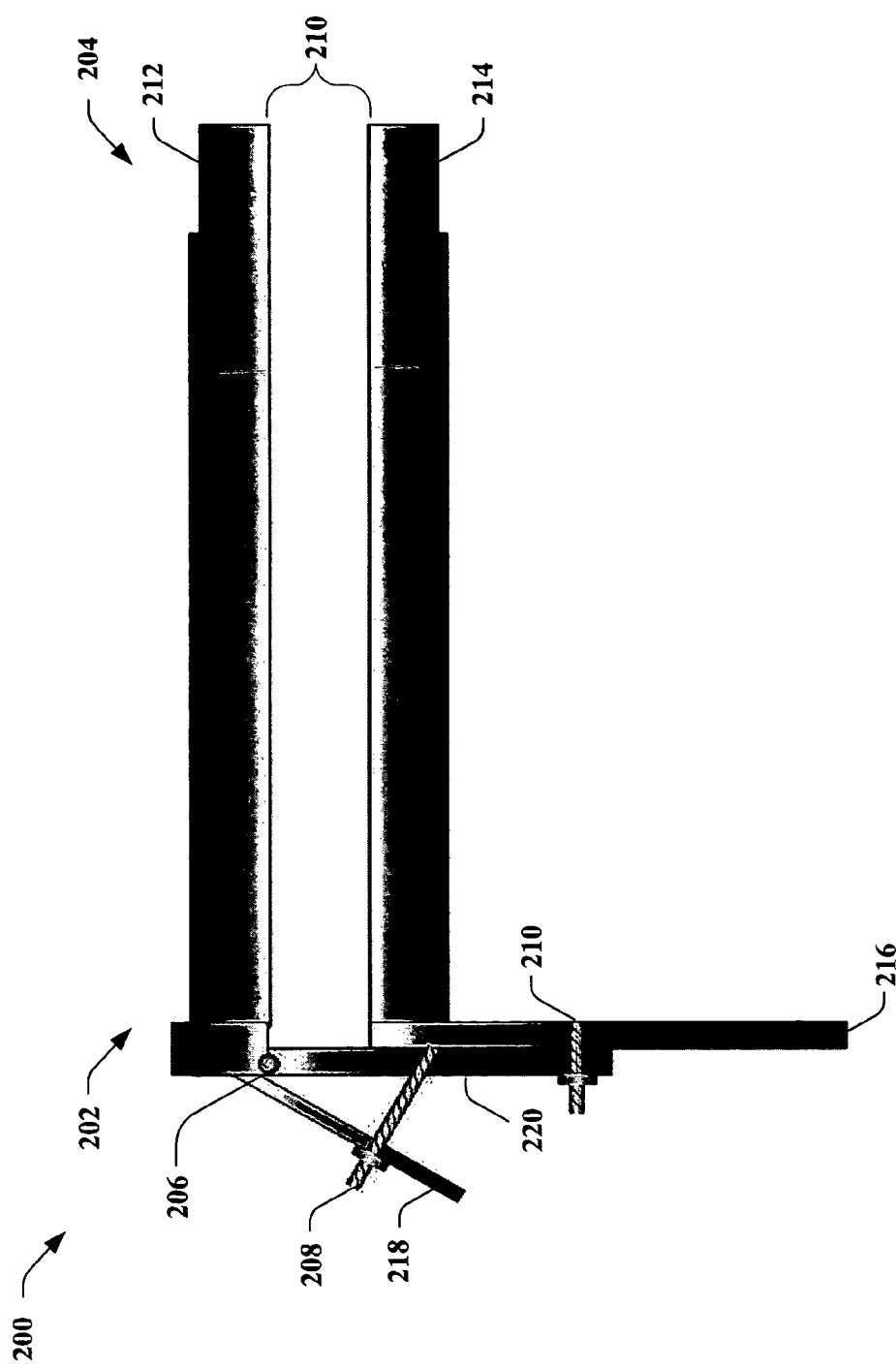

As illustrated in FIG. 3, the two halves of the cylinders 212 and 214 can be variably expanded equally at both proximal end 202 and distal end 204. As illustrated, a movable U-shaped handle 220 is capable of being moved upward moving the top hemi-cylinder 212 upward in a similar fashion and away from lower hemi-cylinder 214. This movement allows an expanded field of vision 210.

The hinged cylinder retractor 200 further includes two locking screw nut mechanisms 208 and 210 that provide a means to prevent the expanded retractor from collapsing from its expanded position, thus mitigating unwanted movement. A first locking screw nut mechanism 208 is located on the upper cylinder handle 218. A second locking screw nut mechanism 210 interlocks the lower 90-degree handle 216 to the upper-hinged U-shaped handle 220. A ratchet locking mechanism may be alternatively used in place of the locking screw nut mechanism.

Figure 4:
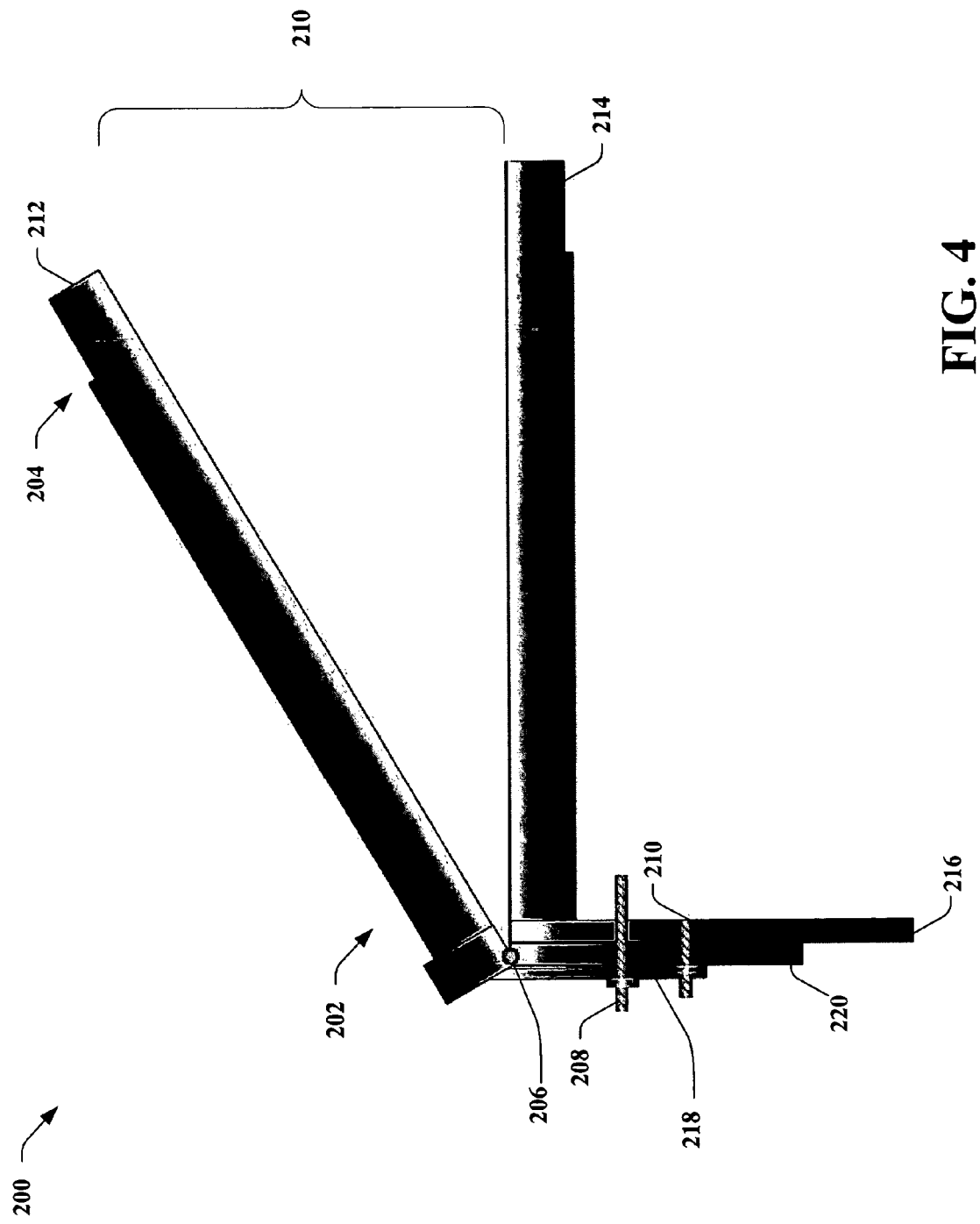

According to another aspect illustrated in FIG. 4, the distal end 204 of the upper hemi-cylinder 212 can be expanded while the proximal end 202 is hinged and not expanded. The upper hemi-cylinder 212 pivots upon the hinges 206 allowing the distal end 204 to move up and away from the lower hemi-cylinder 214 while the proximal ends 202 of the upper and lower hemi-cylinders 212 and 214 remain in contact with each other. In this position, both locking screw nut mechanisms 208 and 210 (or ratchet locking mechanisms) are parallel and engaged in close proximity to each other to prevent movement of the upper and lower hemi-cylinders 212 and 214, maintaining them in a safe and secure manner. In this position, the field of view 210 is expanded and much larger than the field of view illustrated in FIG. 3 where the hemi-cylinders 212 and 214 are expanded equally at both proximal end 202 and distal end 204.

Figure 5:
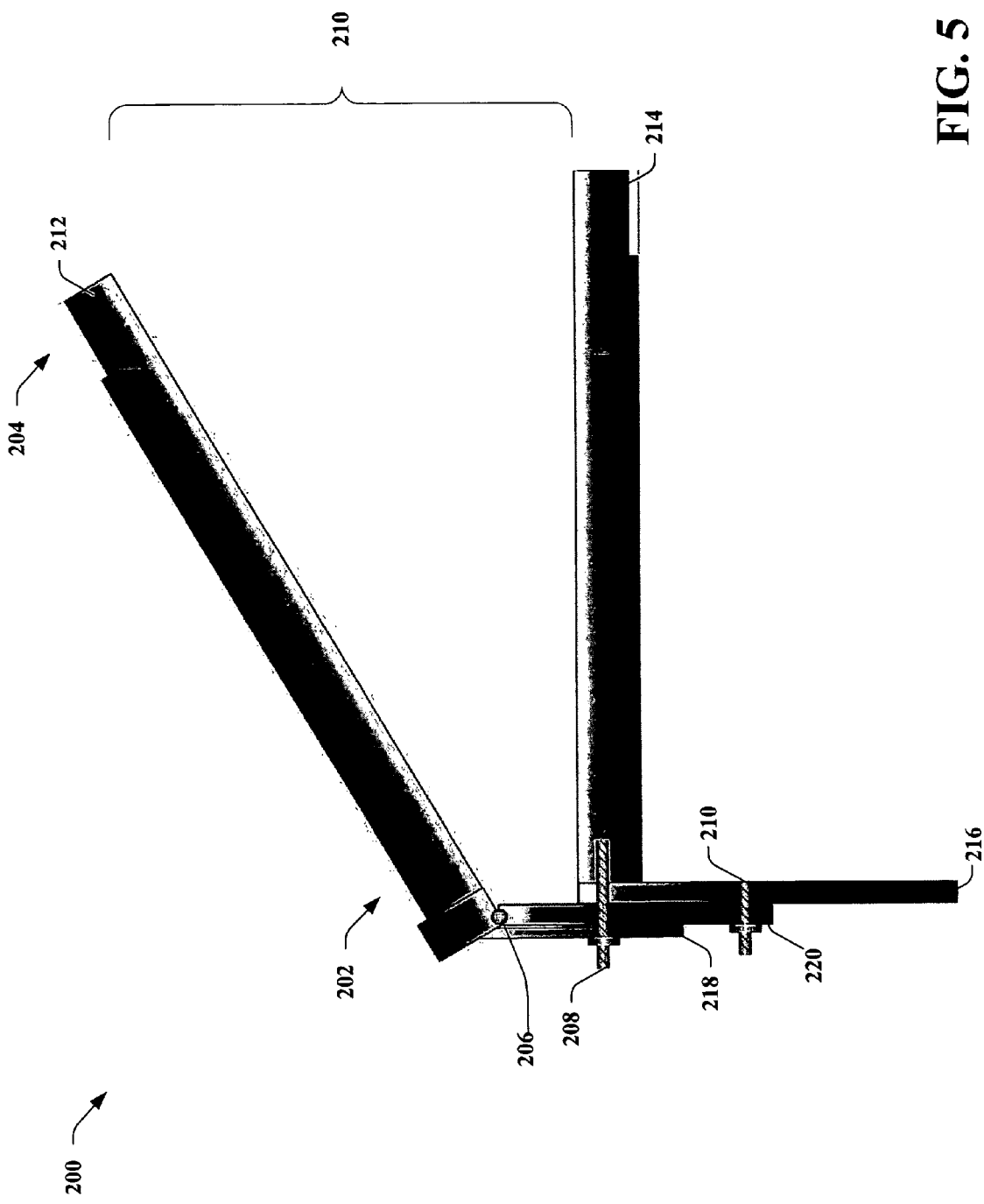
Figure 6:
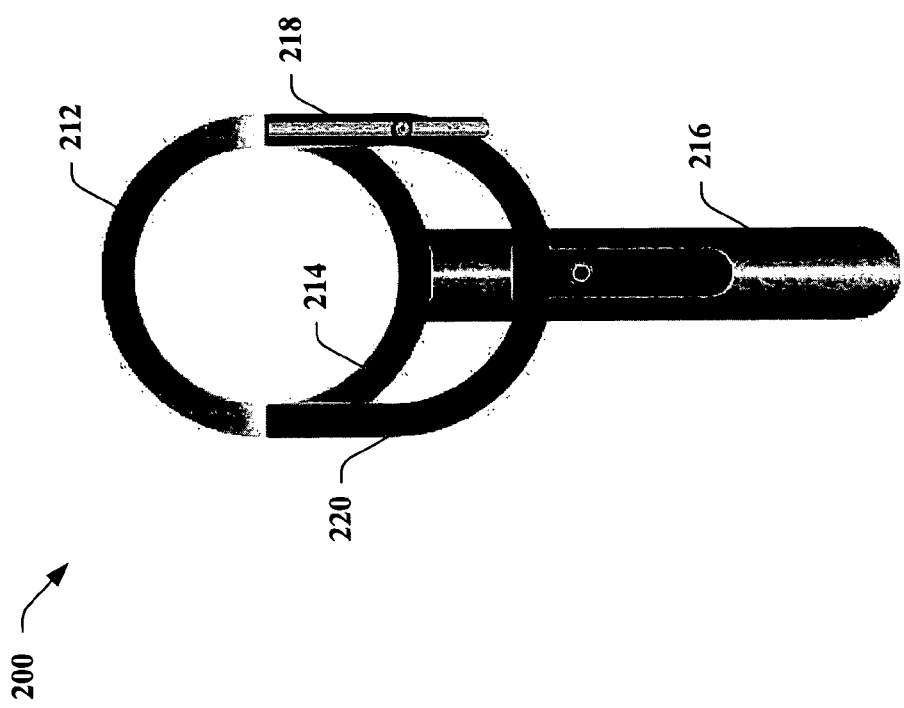

FIG. 5 illustrates an alternate embodiment allowing for a maximum exposure or maximum field of vision 210. In this embodiment, the hemi-cylinders 212 and 214 are expanded equally at both the proximate end 202 and the distal end 204, similar to the movement described with reference to FIG. 3. Thus, the handle 220 is moved in an upward direction, or toward the upper hemi-cylinder 212, pushing the upper hemi-cylinder 212 up and away from the lower hemi-cylinder 214.

Additionally, the upper hemi-cylinder 212 is pivoted at pivot points or hinges 206, similar to the movement described with reference to FIG. 4. While in the position illustrated in FIG. 5, the locking screw nut mechanisms 208 and 210 are parallel to each other and engaged at a distance further away from each other than when the upper hemi-cylinder 212 is simply pivoted as illustrated in FIG. 4. This larger distance is caused by the movement of the upper hemi-cylinder 212 up and away from the lower hemi-cylinder 214 and, likewise, the upper hemi-cylinder handle 218 to which the first locking screw nut mechanism 208 is operatively attached. The locking screw nut mechanisms 208 and 210 are engaged to prevent movement of the upper and lower hemi-cylinders 212 and 214, providing safety by mitigating unwanted movement.

According to another embodiment, a smaller retractor oriented at a right angle to and placed within a larger retractor can allow for even greater bi-directional field of vision. Additionally and/or alternatively, retractors 212 and 214 can be fitted with an endoscopic camera (not shown) and/or a fiber optic light source (not shown) for direct visualization.

Figure 7:
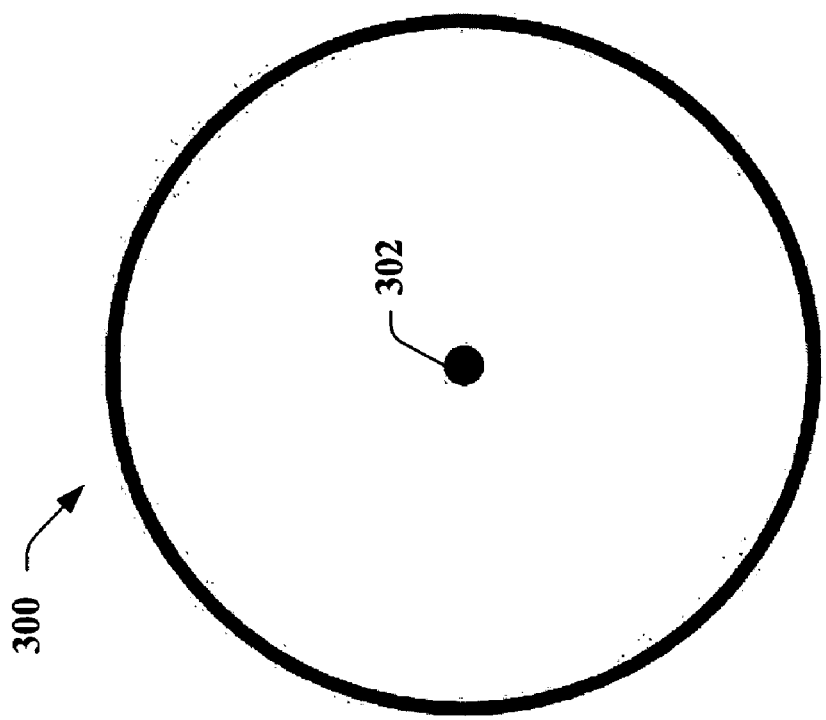
FIGS. 7-12 illustrate exemplary instruments of a screw preparation system according to an aspect of the invention.

With reference now to FIGS. 7-12, illustrated are instruments of a screw preparation system consisting of an awl, a hand-held drill or tap, a ball-tipped probe, a cannulated depth gauge ruler and a hexagonal screwdriver. It is to be understood that the invention is described and depicted in connection with use of various off the shelf components (e.g., awl, drill, screws, . . . ) to facilitate understanding of the novel aspects of the invention—it is to be appreciated that the invention is not limited to any particular type or brand of component and that any suitable components in accordance with the invention can be employed. Alternatively and/or additionally, the instruments can be cannulated to allow for passage over a guide pin or wire. FIG. 7 illustrates a targeted guide 300 that is located in the based end of a radiolucent handle of each instrument of the screw preparation system. A radiolucent handle is transparent to x-rays and other radiation allowing x-rays to pass though and appearing as a dark area on a radiograph. The center 302 of the targeted guide 300 is oriented along the central, longitudinal axis of each respective instrument. Additionally, a guide sleeve with an extended offset is utilized with the screw preparation instruments, as discussed with reference to FIG. 12.

Figure 8:
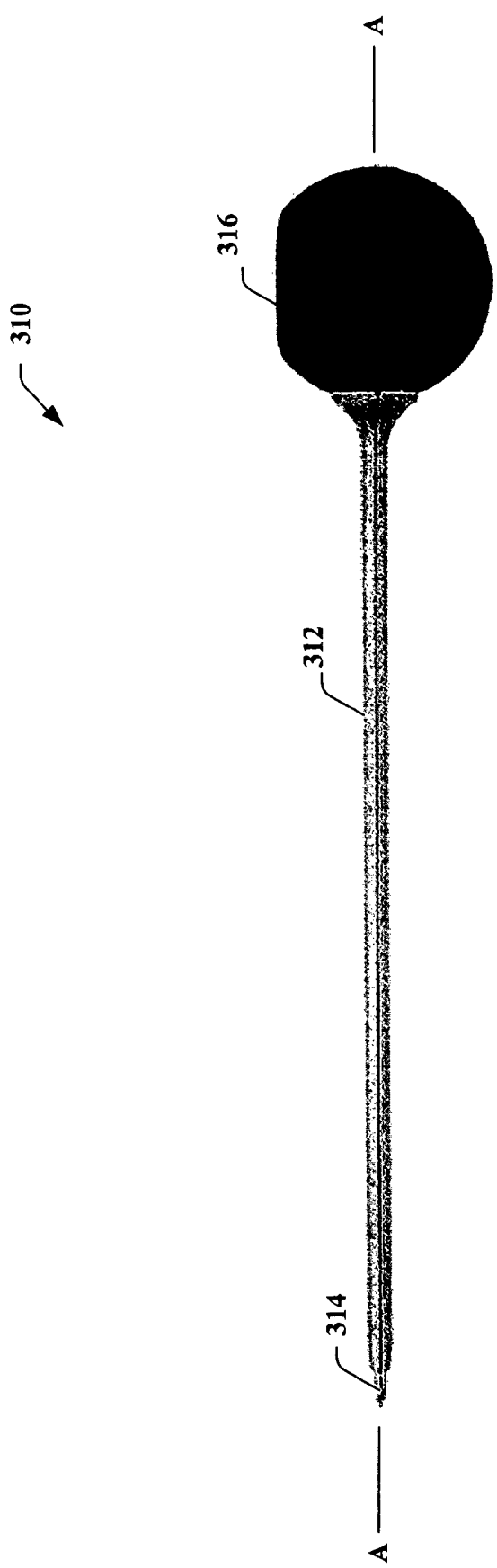

FIG. 8 illustrates an exemplary awl 310 that is an instrument utilized in conjunction with the screw preparation system. The awl 310 is employed for alignment purposes and has a larger diameter metal shaft 312 that is round in cross-section. The shaft 312 is relative to a smaller diameter tip 314 that is pointed allowing for controlled entry point placement. The awl handle 316 is spherical and made of a radiolucent material (e.g. carbon) and is marked with a targeting guide, as illustrated and discussed with reference to FIG. 7, oriented along the central axis A of the awl shaft 312.

Figure 9:
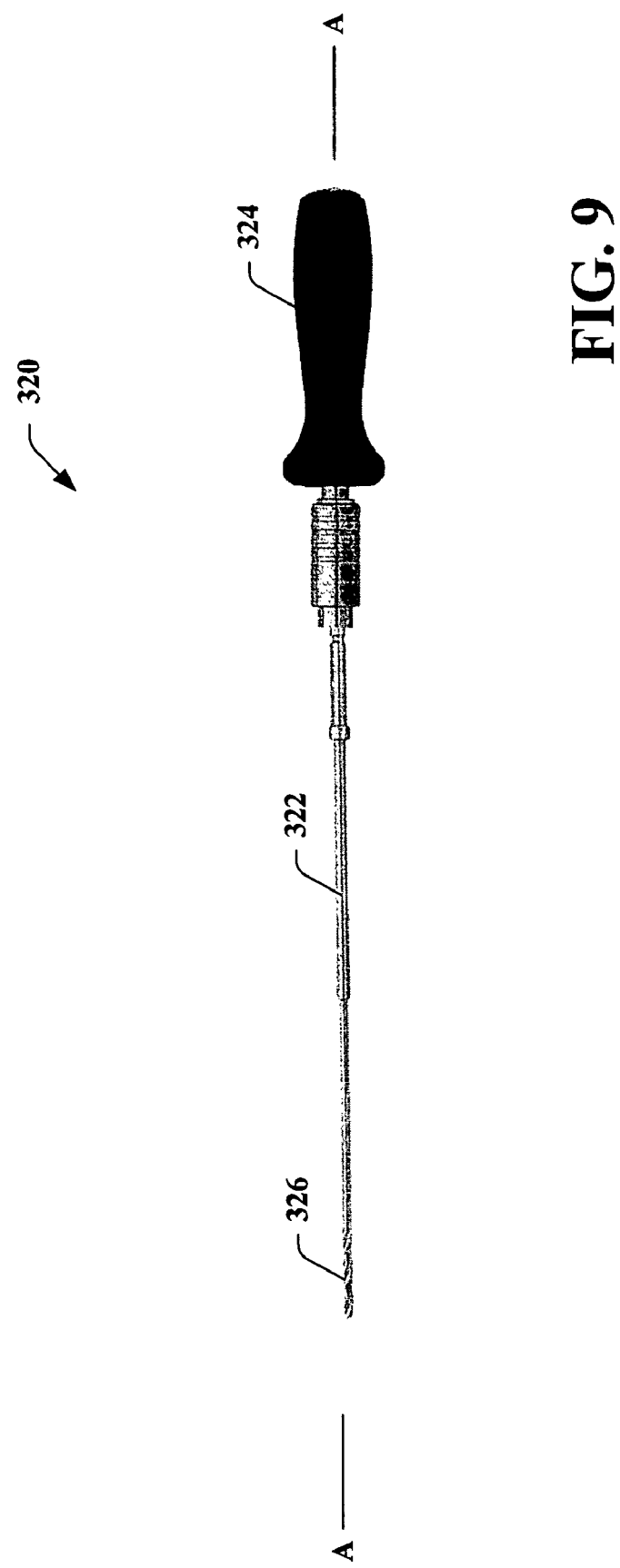

FIG. 9 illustrates an exemplary hand-held drill 320 (or tap) that is an instrument of a screw preparation system. The hand-held drill 320 (or tap) has a metal shaft 322 with a radiolucent handle 324 and a drill tip 326 (or tap tip). The handle 324 is marked with a targeting guide, as illustrated in FIG. 7, oriented along the central axis A of the drill shaft 322. The outer shaft of the drill or tap may be labeled with a ruler or marking guide. The drill or tap may be cannulated to fit over a guide pin or wire.

Figure 10:
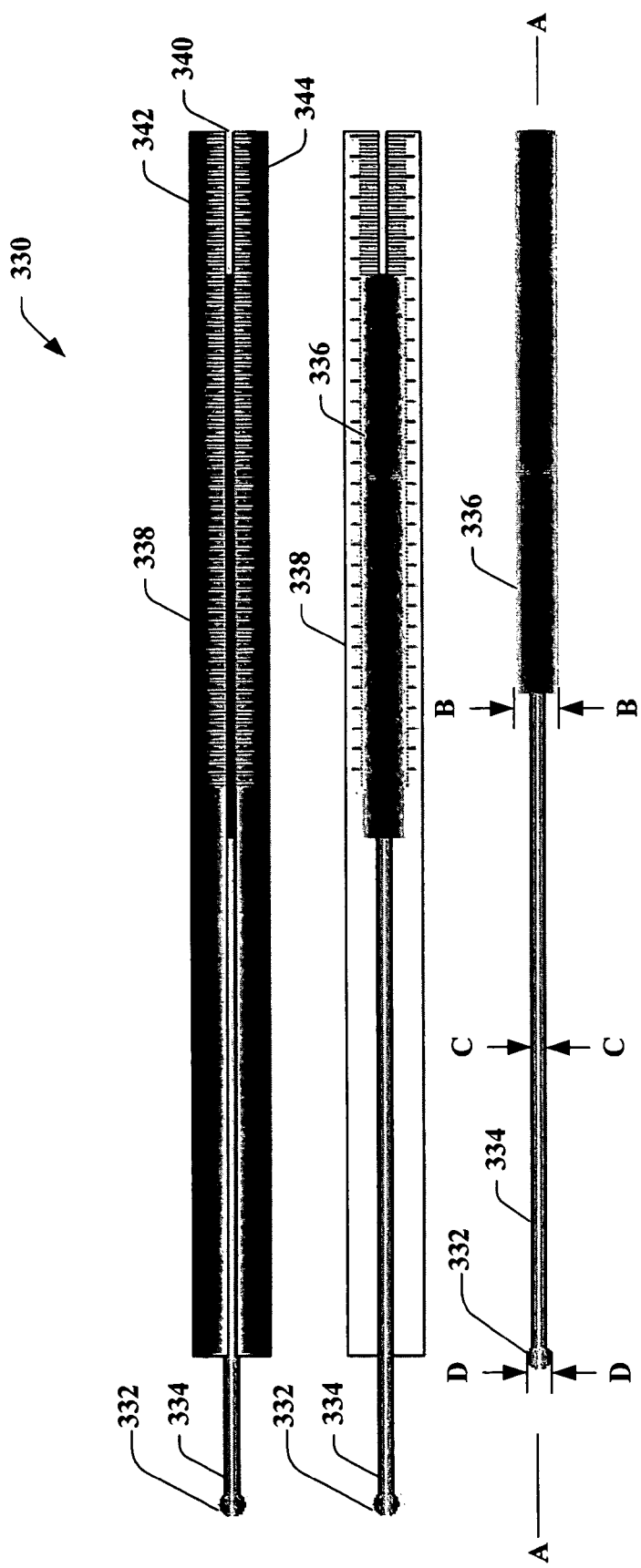

FIG. 10 illustrates three views of an exemplary ball-tipped probe 330 that is another instrument of the screw preparation system. The bottom figure is a view of the ball-tipped probe 330, the middle figure is a cross sectional view of the ball tipped probe 330 with a depth gauge ruler, and the top figure is the probe with a depth gauge ruler in full view. The ball-tipped probe 330 has a metal ball 332 at its tip, a metal shaft 334, and a radiolucent handle 336 marked with a targeting guide, as illustrated in FIG. 7, oriented along the central axis A of the probe shaft 334.

As shown with respect to the bottom figure, the handle diameter, B, is greater than the shaft diameter, C, and the ball tip diameter, D, is greater than the shaft diameter C. The cross-sectional shape of the tip, shaft, and handle are round. A cannulated depth gauge ruler 338 fits over the ball-tipped probe. The metal ruler 338 has a fluted opening 340, shown in the top figure, to allow for visualization of the ball-tipped probe 330 within the cannula. Both sides of the fluted opening 342 and 344 are marked with measurements to assess the depth of the drill path. The measurement is determined using the base of the ball-tipped probe 330.

Figure 11:
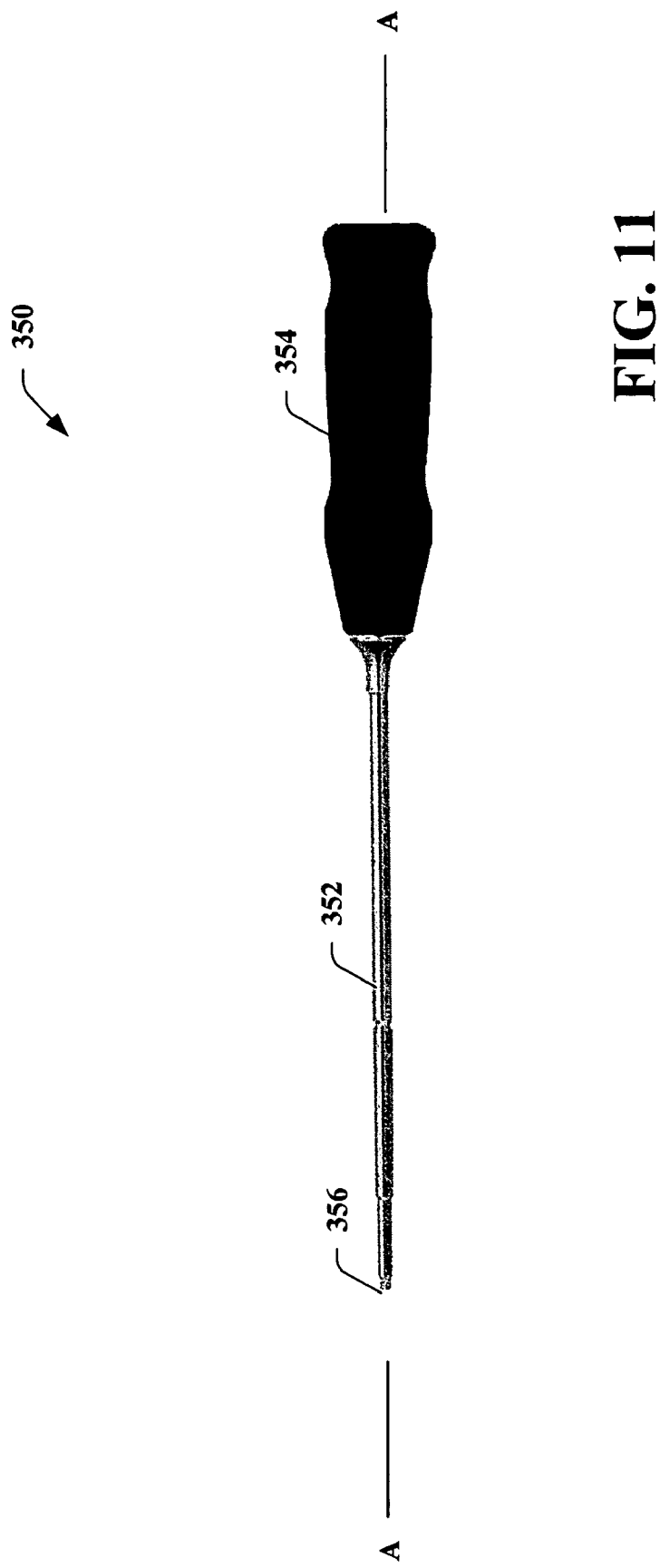

Referring now to FIG. 11, illustrated is a hexagonal screwdriver 350 that has a metal shaft 352 and a radiolucent handle 354. The hexagonal screwdriver handle 354 is marked with a targeting guide oriented along the central axis A of the screwdriver shaft 352, as discussed with reference to FIG. 7. The screwdriver tip 356 is hexagonal and the cross sectional shape of the shaft 352 is round. The diameter of the screwdriver is wide enough to engage a locking mechanism when inserted into a T-handle alignment guide, discussed in further detail below. The screwdriver 350 may be cannulated to fit over a guide pin or wire.

Figure 12:
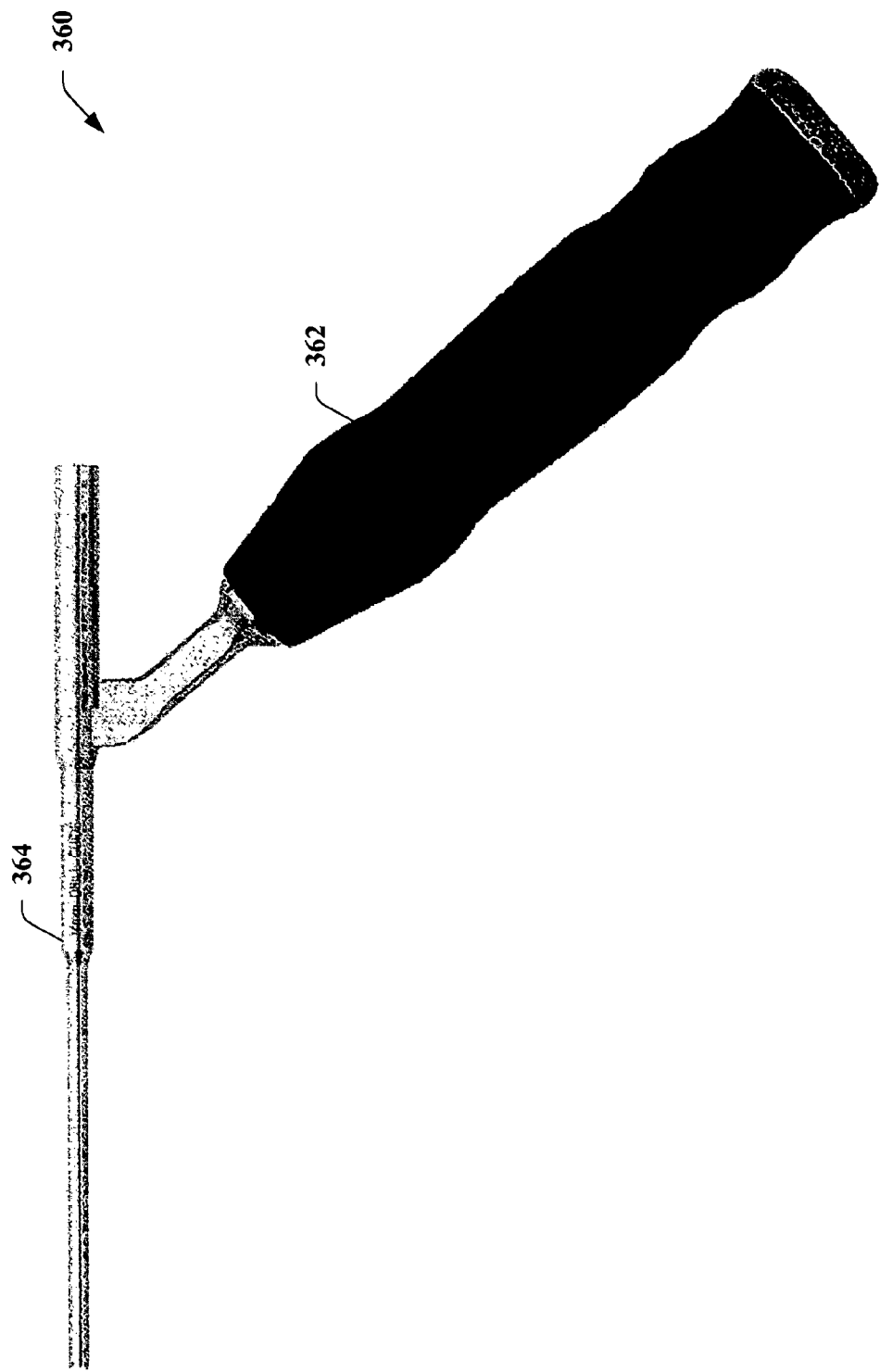

FIG. 12 illustrates a guide sleeve 360 with an extended offset that is employed with the screw preparation instruments. The guide sleeve 360 has an extended offset handle 362 angled 45 degrees from the axis of the sleeve 364. The handle 362 is radiolucent and capable of accommodating different sized guide sleeves 364 to accommodate the awl 310, hand-held drill 320, ball-tipped probe 330, and hexagonal screwdriver 350. The guide is utilized for soft tissue protection, instrument guidance, and minimization of radiation exposure.

Referring now to FIG. 13, illustrated is a front and side view of a polyaxial screw 400 with rod-guidance entry face 402 and two alignment holes 404. One of the two alignment holes 404 can be seen in the side view and the other alignment hole is on the other side of the screw directly opposite the first alignment hole 404. The rod-guidance entry face 402 is located on the open face of the polyaxial head 406 and act as a funnel 408 to optimize guidance of a spinal rod, shown in FIG. 15, through the open face. The diameter of the funnel 408 decreases proximally to a diameter no less than the diameter of a spinal rod, allowing the spinal rod to fit securely within the funnel opening. The screw 400 can further be cannulated with an opening though the long axis of the screw 400 to allow for placement over a guide pin or wire.

The true screw head 406 matches the hexagonal screwdriver 350, discussed with reference to FIG. 11. The polyaxial screw design allows for at least about 45 degrees of angulation in all directions. The pitch, core diameter, and outer diameter of the screw shank 412 can be cortical or cancellous in design and the screw tip 410 is self-tapping. The diameter and length of the screw is variable allowing for variations in the bony anatomy of the cervical, thoracic, lumbar, and sacral spines.

The polyaxial screw 400 is utilized with a T-handle alignment guide, which will be discussed in more detail below. Without the T-handle alignment guide, the polyaxial head 406 is open slotted, as shown in FIG. 13, from about the 11 o'clock position 414 to about the 1 o'clock position 416 and a rod may, therefore, be top loaded into the screw head 406, shown by the direction of arrow A. It is to be understood that the funnel 408 can be placed on the guide itself and not on the screw. In such a way, a screw without the funnel 408 can be employed according to an aspect of the invention.

Figure 14:
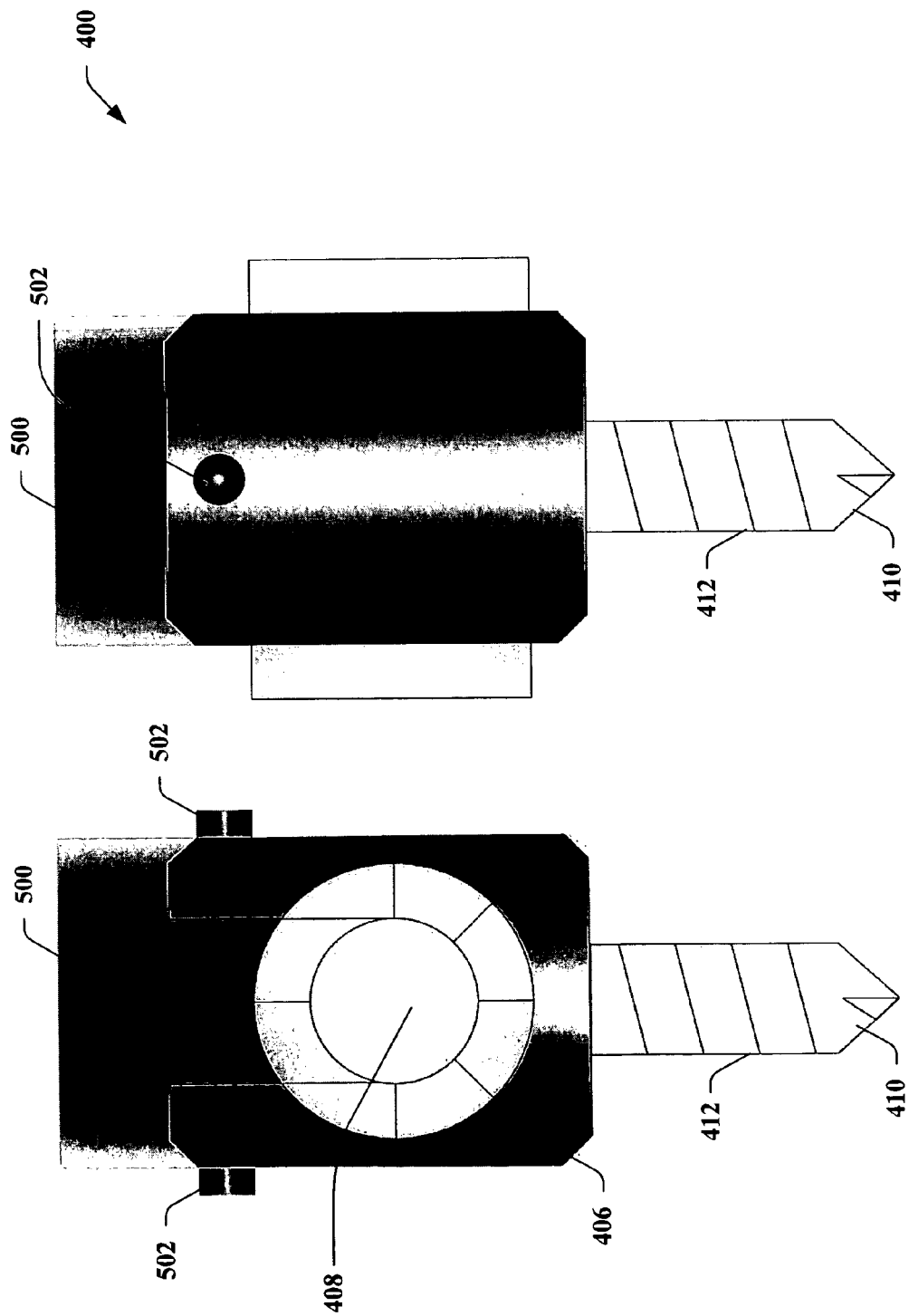

FIG. 14 illustrates a front and side view of a polyaxial screw 400 with a T-handle alignment guide 500 in place in the screw head 406. The T-handle alignment guide 500 is placed into the screw head 406 and secured or trapped in place with two locking mechanisms 502 that extend through or from one side to the other side of the two alignment holes 404. The alignment holes 404 are located on the closed faces of the polyaxial head 406 and are oriented 90 degrees in relation to the open face of the polyaxial head 406. As illustrated in FIG. 14, the holes 404 accommodate the locking mechanisms 502 of the T-handled alignment guide 500. It will be understood by those skilled in the art that other means of securing the T-handle alignment guide 500 and the screw 400 can be utilized and are within the scope of the invention. For example, a screw mechanism on either side can be utilized wherein matching screws on the distal end of the T-handle alignment guide and the proximal end of the polyaxial screw head are tightened, securing the T-handle alignment guide 500 and the screw 400 together. With the T-handle alignment guide 500 in this position, the funnel entrance 408 is round in shape and accommodates front entry of a rod.

Figure 15:
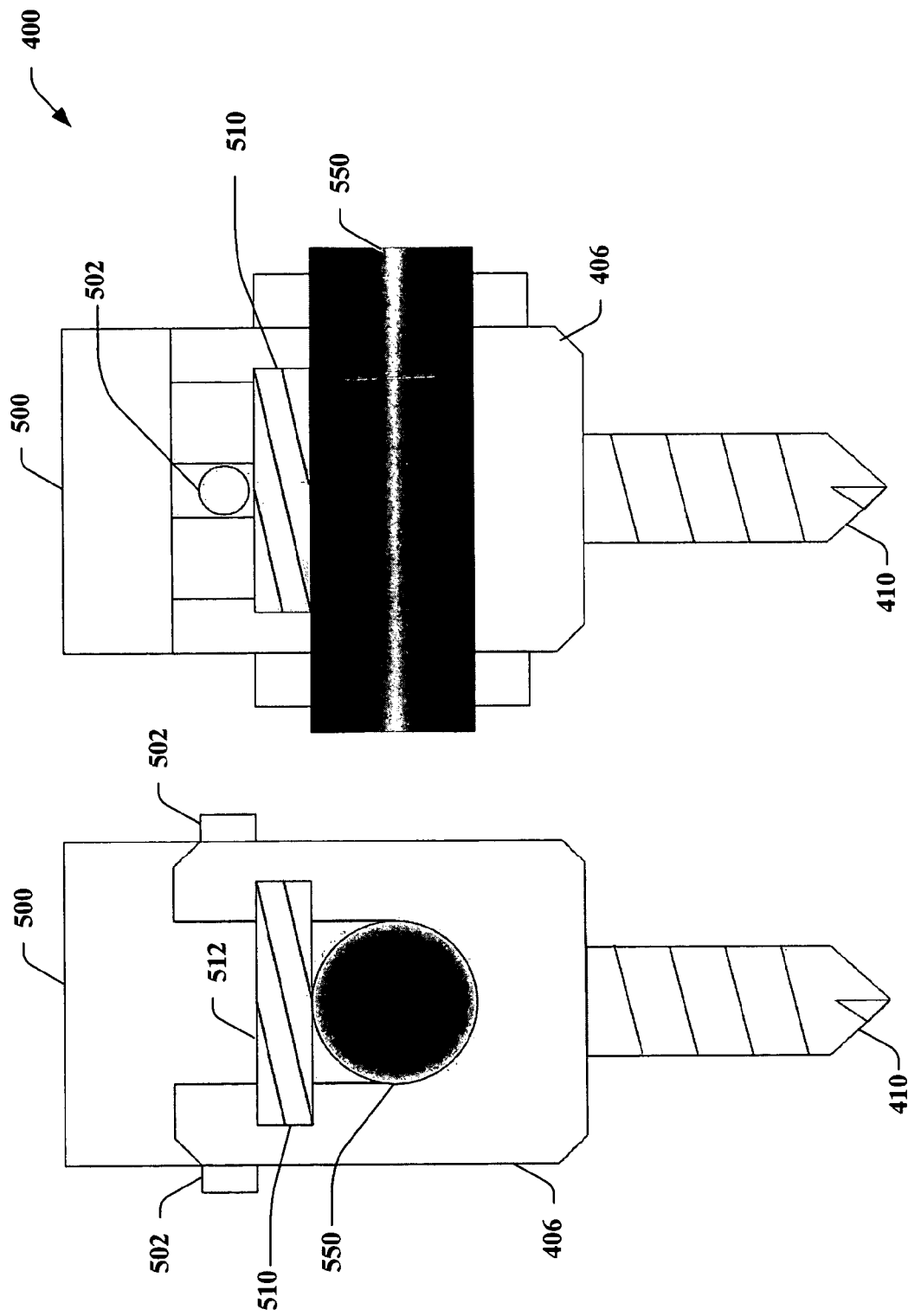

Referring now to FIG. 15, illustrates is a front and side view of a polyaxial screw 400 including a setscrew 510 securing a rod 550 in the polyaxial head 406. The outer threads of the setscrew 510 match the inner threads within the polyaxial head 406. The top 512 of the setscrew accommodates a hexagonal screwdriver 350, illustrated in FIG. 11. As the setscrew 510 is tightened, the rod 550 is seated securely within the saddle of the polyaxial head 406.

With reference now to FIGS. 16-23, illustrated is a rod guidance system according to an aspect of the invention. The rod guidance system includes a rod with a tapered tip, a T-handle rod holder, a T-handle alignment guide, an alignment marker sleeve, a flexible alignment marker with a polyaxial head, and a malleable template rod.

Figure 16:

Initially referring to FIG. 16, illustrated is a rod 600 that includes a tapered-tip end 602 to allow for safe and easy passage through soft tissues. The cross-sectional shape of the rod is round and the composition can be titanium, stainless steel, or the like. The rod is employed in conjunction with a polyaxial screw 400, illustrated and discussed with reference to FIGS. 13-15, and/or a transconnecting tower, which will be discussed in more detail below.

Figure 17:
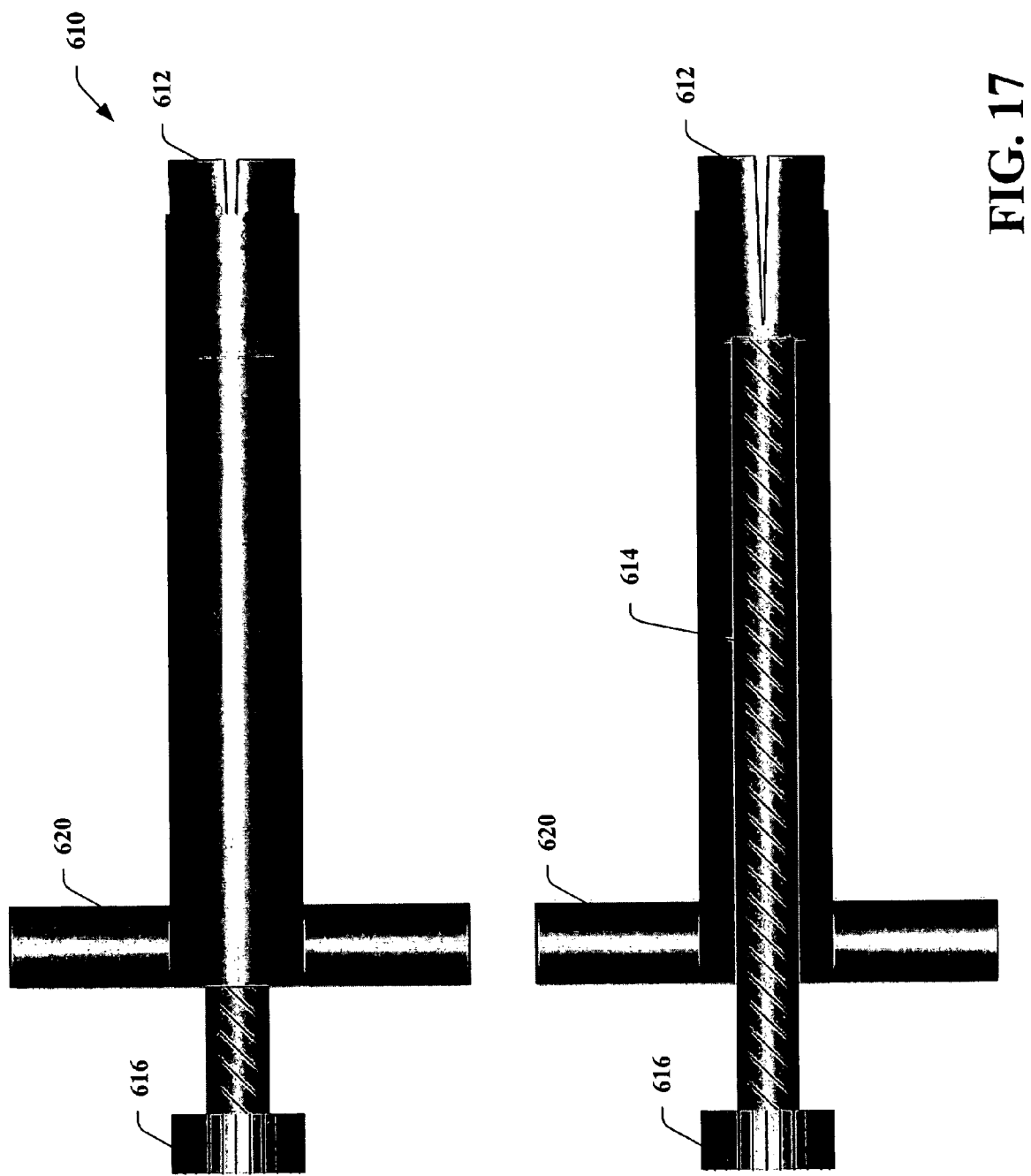

When placed longitudinally through polyaxial screw(s), the arrow rod is referred to as a spinal rod. When placed transversely through a transconnecting tower(s), it is referred to as a connecting rod. The rod 600 can be contoured to fit through the rod-guidance entrance of the polyaxial screw(s) or transconnecting tower(s). The rod(s) 600 functions to link the polyaxial screws and transconnecting tower together as one unit. When a set screw is tightened, the rod seats securely within the saddle of the polyaxial head or transconnecting tower FIG. 17, illustrates a rod holder 610 with a cut-away view shown at the bottom of the figure. The rod holder 610 holds the arrow rod 600 at its base and is utilized to guide the leading end of arrow rod 600 through the polyaxial screws 400. The rod holder 610 is designed to systematically secure, control, and release the rod 600. The tip of the holder 612 is cylindrical in shape when in the closed or locked position. The tip 612 opens up similar to two hemi-cylinders in the open or unlocked position. The diameter of the closed cylinder tip 612 is less than the diameter of the arrow rod 600. The closing mechanism is engaged with a long screwing mechanism 614 that draws the open hemi-cylinders into the chamber of the holder, thereby closing the hemi-cylinders and securing the base of the arrow rod into the inner cylinder tip of the holder.

A dial 616 at the base of the rod holder 610 controls the opening and/or closing mechanism. Turning the dial 616 in a counter-clockwise direction draws in and closes the cylinder tip 612. Turning the dial 616 clockwise pushes out and opens the cylinder tip 612. The base of the dial is marked with a targeting guide oriented along the central axis of the shaft of the rod holder. A T-handle 620 at the base of the chamber affords greater control of the rod holder 610. Different sized rod holders 610 may be employed for different sized rods 600.

Figure 18:
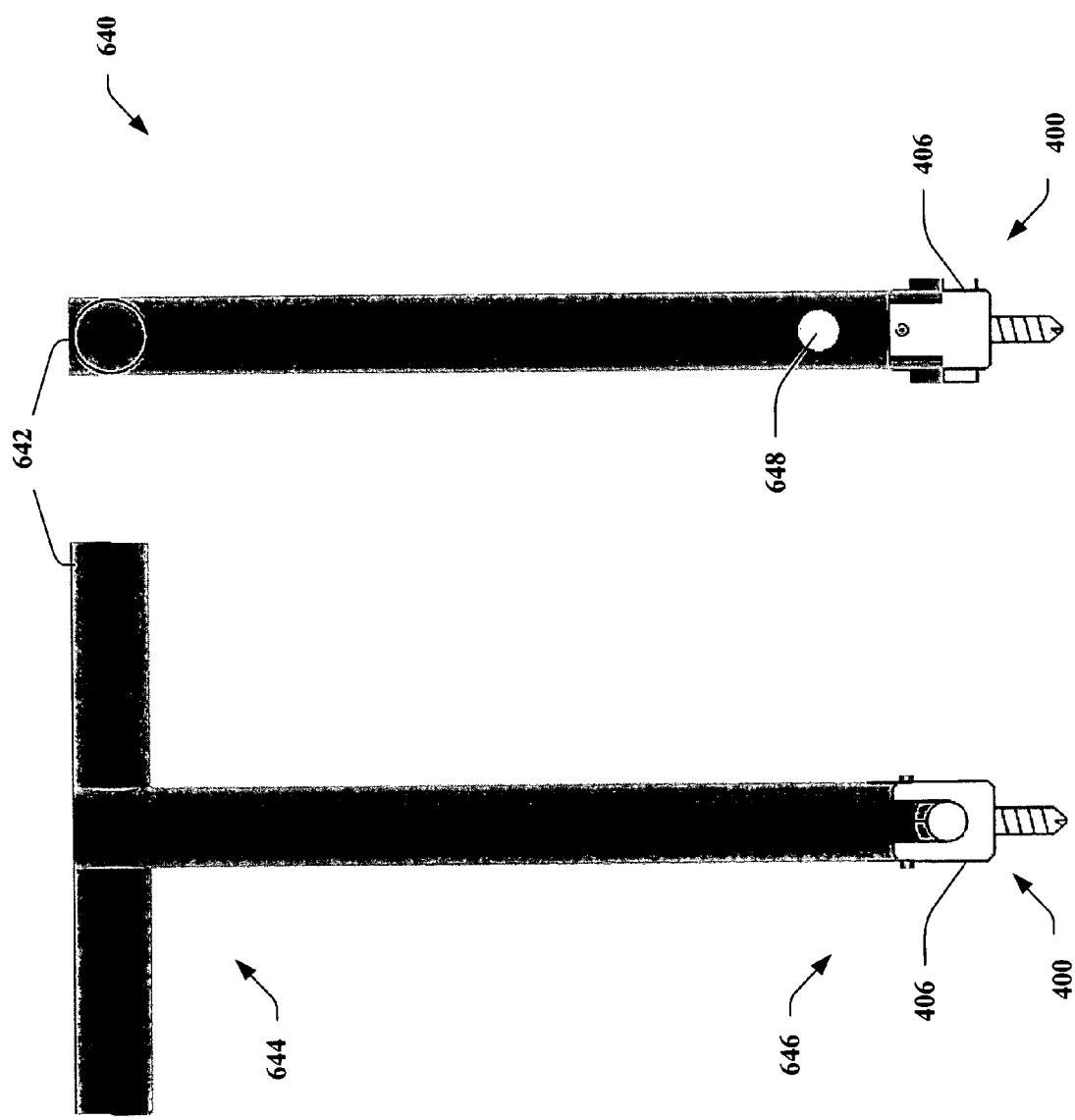
Figure 19:
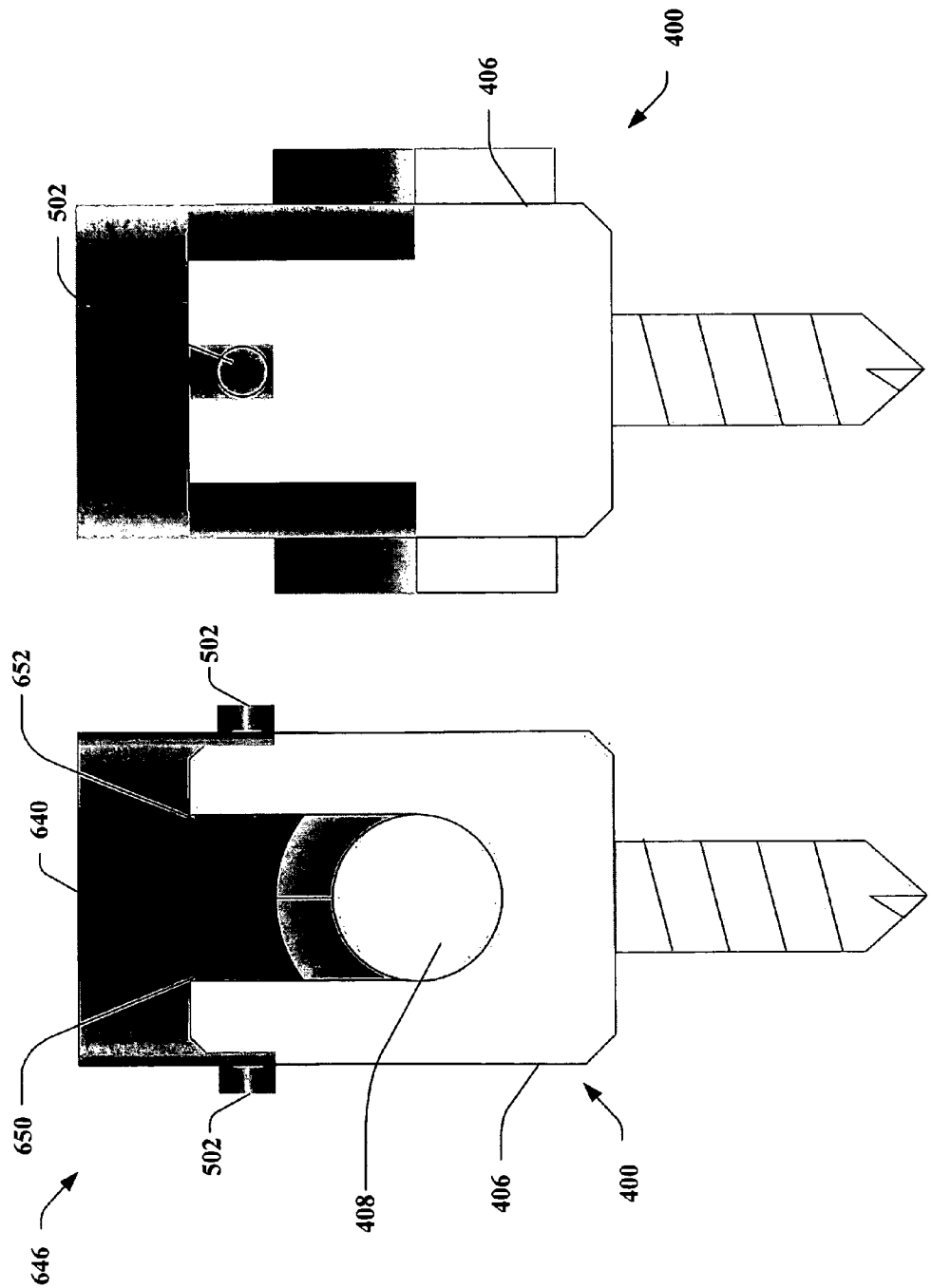

With reference now to FIGS. 18, 19 and 20 aspects of a T-handled alignment guide 640 is illustrated in front and side views. The T-handled alignment guide 640 is utilized to control the polyaxial screw head 406 and to guide placement of the setscrew 400. The T-bar 642 is located at the base 644 of the alignment guide 640. The distal face 646 is perpendicular to the upper T-bar 644 and matches the open face of the rod-guidance entry slot of the polyaxial head 406, as illustrated in FIG. 19. The distal face 646, located at about the 11 o'clock 650 to about the 1 o'clock position 652, contains the upper section of the spinal rod guidance funnel 408. The distal end of the T-handled alignment guide may be fitted with a complete rod guidance funnel to facilitate the safe passage of spinal rods through pedicle screws without rod guidance funnels.

A locking mechanism 502 is located parallel to the upper T-bar 644 and matches up with the alignment holes 404 on the closed faces of the polyaxial head 406. As illustrated in FIG. 20, the locking mechanism 502 can be composed of two small pegs 512 attached to respective lever arms 514 recessed within the distal chamber 646 of the alignment guide 640. As the alignment guide 640 is inserted or placed into the screw 400, the two pegs 512 and/or respective lever arms 514 are pushed inward or toward each other. When the alignment marker sleeve or the hexagonal screwdriver is fully seated within the inner chamber of the T-handle alignment guide 640, the locking mechanism 502 is activated and the pegs 514 are displaced laterally through the alignment holes of the screw 404. It will be appreciated by those skilled in the art that other types of locking mechanisms can be utilized in accordance with the invention (e.g., matching screws).

Referring once again to FIG. 18, two round alignment windows 648 are present above both locking mechanisms 502 to facilitate fluoroscopic assessment of orientation of the alignment guide 640 during surgery.

Figure 21:
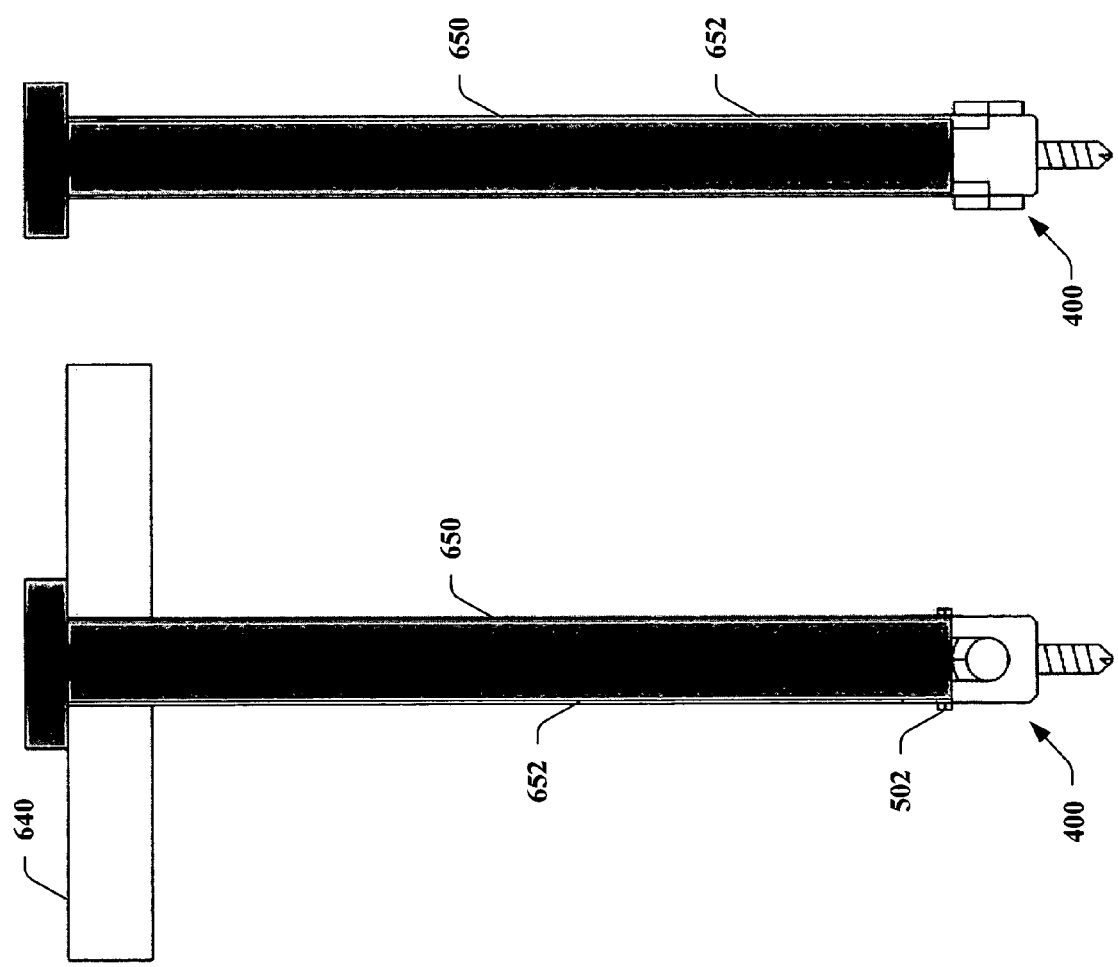

FIG. 21 illustrates front and side views of an alignment marker sleeve 650 that fits into the inner cylindrical chamber 652 of the T-handle alignment guide 640. The sleeve 650 is cylindrical in shape to match the shape of the T-handle alignment guide 640. The sleeve 650 is cannulated to accommodate a flexible screw alignment marker. An alignment marker entry portal is located at the base of the sleeve. The tip of the sleeve activates the locking mechanism 502 of the T-handled alignment guide 640.

Figure 22:
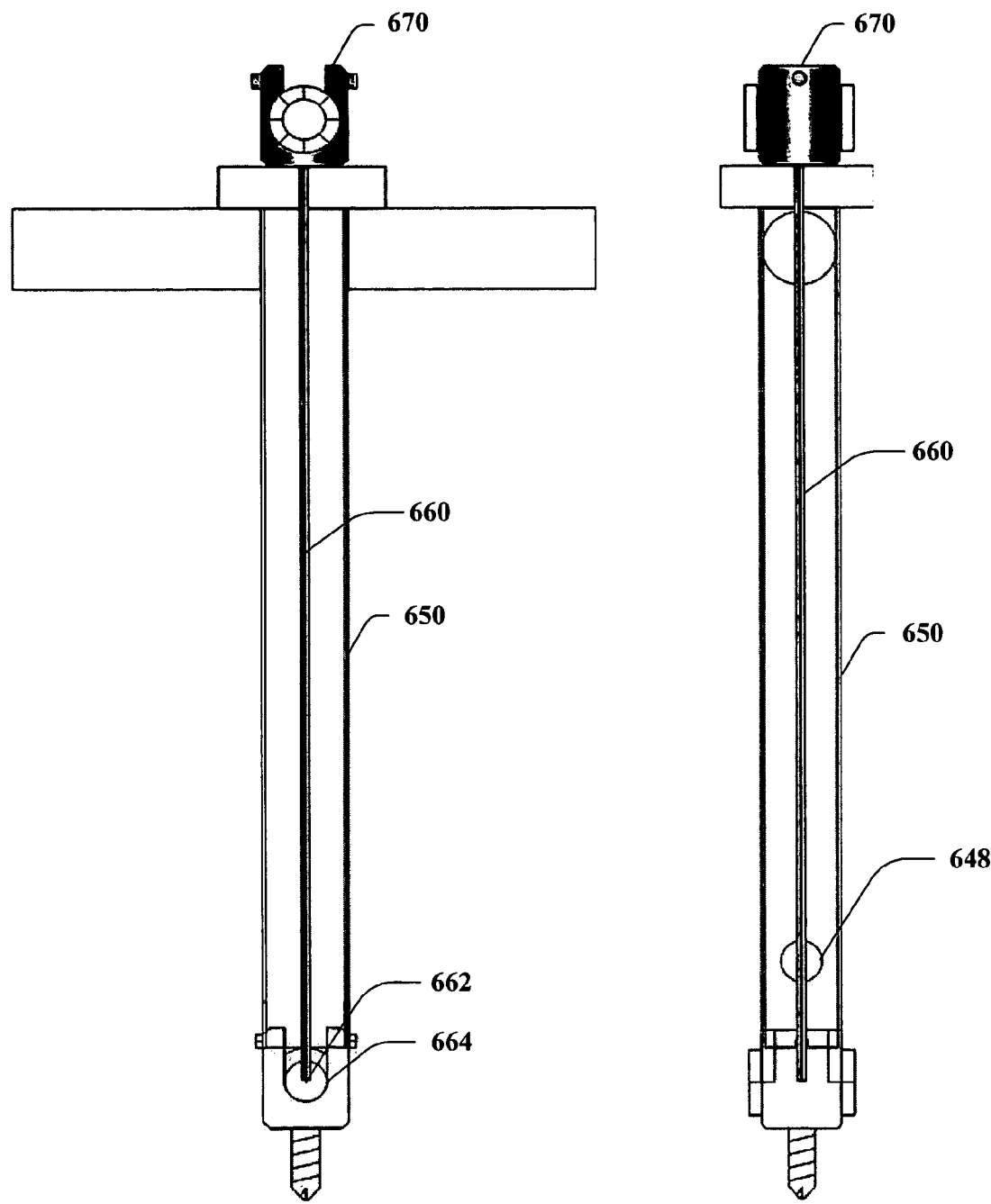
Figure 23:
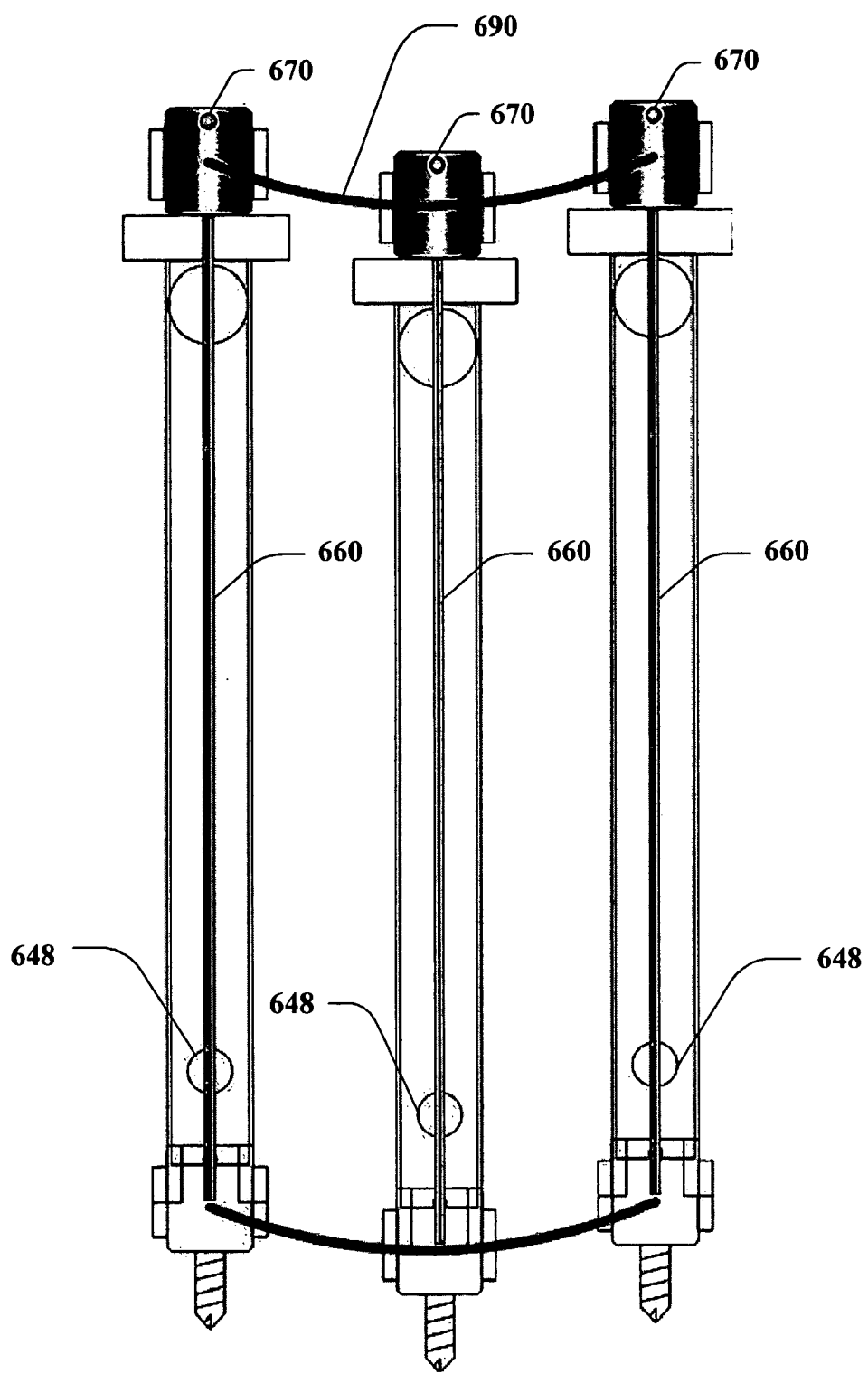
Figure 24:

A flexible screw alignment marker 660 fits within the cannula of the sleeve 650 and has a ruler or other marking means thereon, as illustrated in FIG. 22. The shaft of the marker 660 is composed of a flexible material that maintains its original shape after being subjected to bending forces (e.g. stainless steel wire). The tip of the marker 662 is located at the center of the polyaxial screw head 406 when the marker is fully seated on the sleeve entry portal, as illustrated in FIG. 23. A polyaxial head 670 is located at the top of the marker 660. The polyaxial head 670 accommodates a malleable template rod 690 utilized to connect a series of flexible alignment markers 660. The malleable template rod 690 is illustrated in FIG. 24, is round in cross section, made of malleable metal and covered with a plastic molding, which is also malleable. The connecting system may alternatively be made of a non-malleable material.

Figure 25:
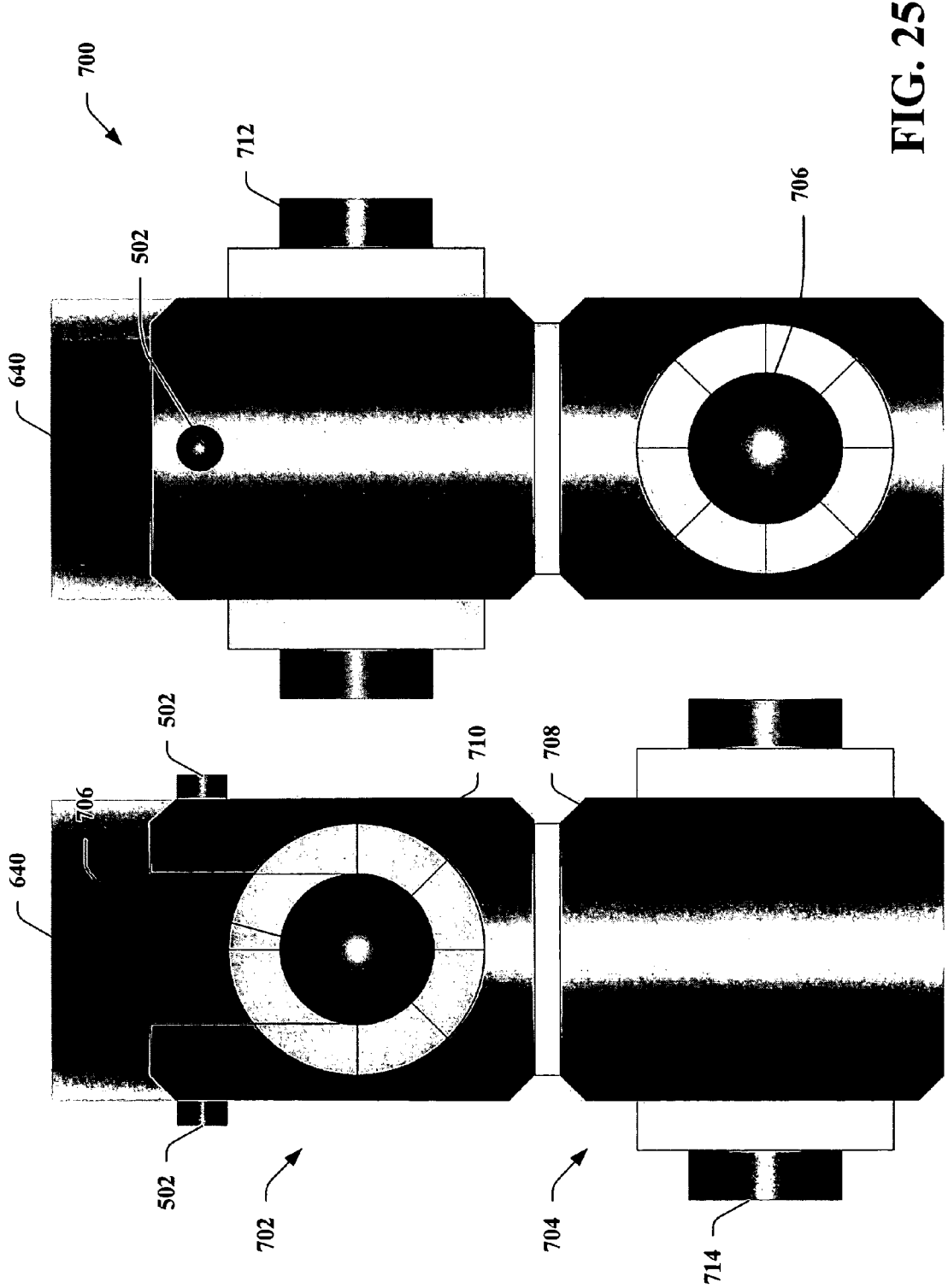
FIGS. 25-26 illustrate a transconnecting tower in accordance with an aspect of the subject invention.
Figure 26:
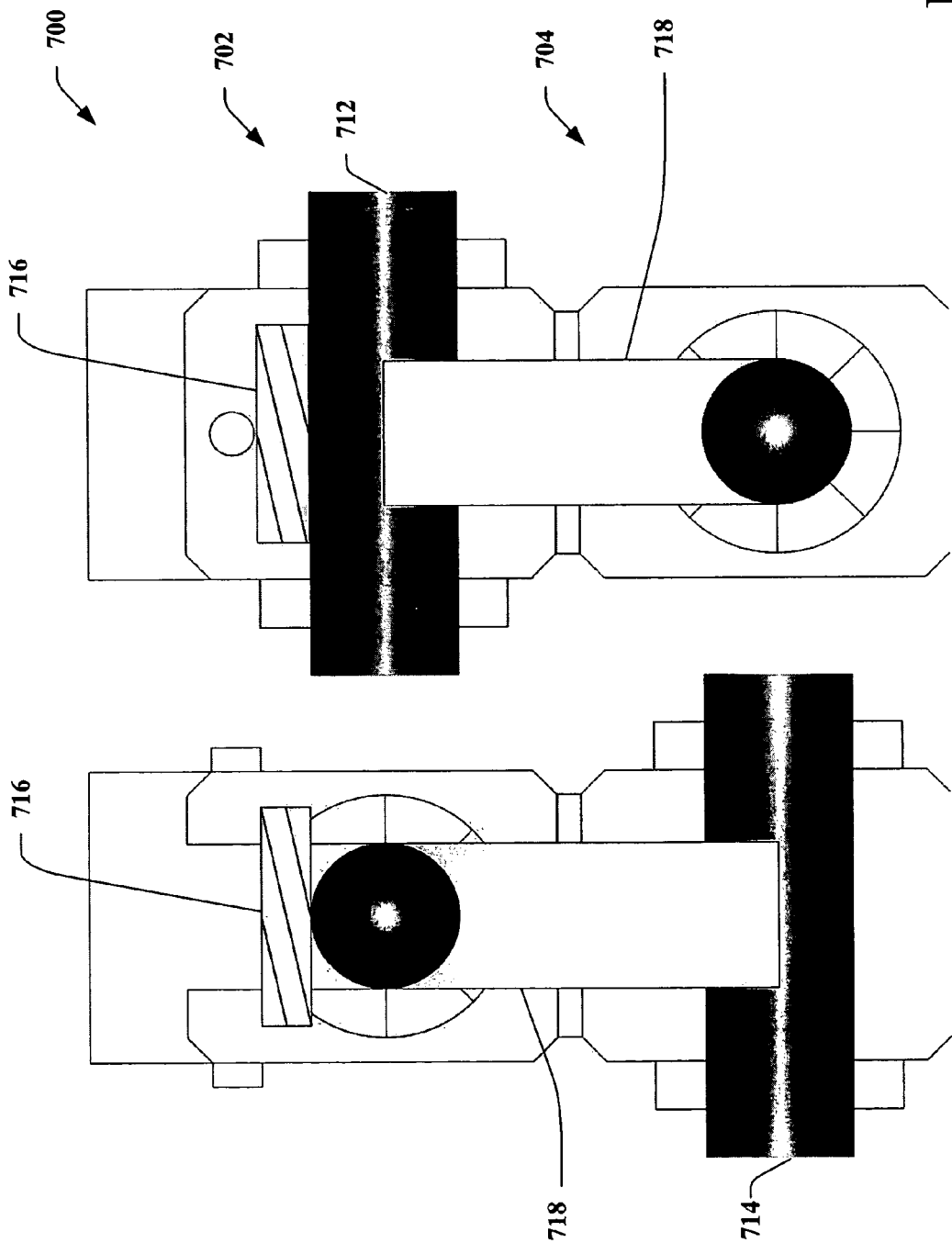

FIGS. 25 and 26 illustrate front and side views of a transconnecting tower 700 with rod-guidance entry slots and alignment guide holes. Both levels of the tower 702 and 704 contain rod-guidance entry funnels 706. The upper level 702 is additionally fitted with alignment holes located on the closed faces 708 and are oriented 90 degrees in relation to the open face 710. The holes, identical to the polyaxial screw head alignment guide holes, accommodate the locking mechanism 502 of the T-handled alignment guide 640. The upper level 702 houses the connecting rod 712, while the lower level 704 houses the spinal rod 714. Alternatively, the lower level may be open on one side to allow for side-loading into an existing spinal rod. As illustrated in FIG. 26, when both rods 712 and 714 are secured, the entire complex is locked with a setscrew 716, which seats the connecting rod 712 to the rod-locking bolt 718. This provides that the spinal rod 714 is seated securely onto its saddle. The rod-locking bolt 718 is oriented perpendicular to both rods and contains saddles at each end of the bolt. The upper level 702 rotates freely relative to the lower level 704, but locks into place once the setscrew 716 is tightened.

Figure 27:
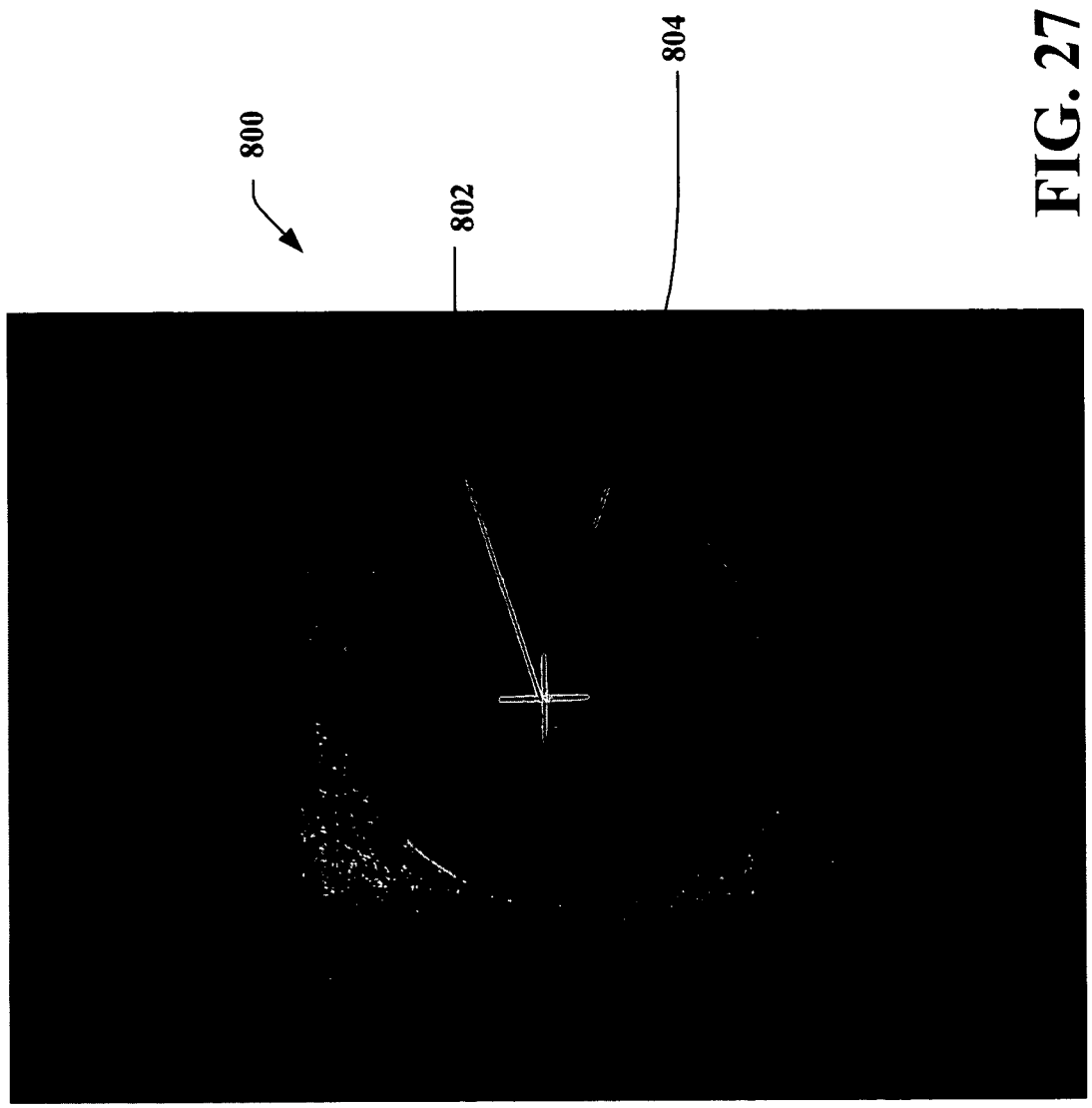
FIGS. 27-29 illustrate a methodology for pedicle localization and approach according to an aspect of the invention.
Figure 28:
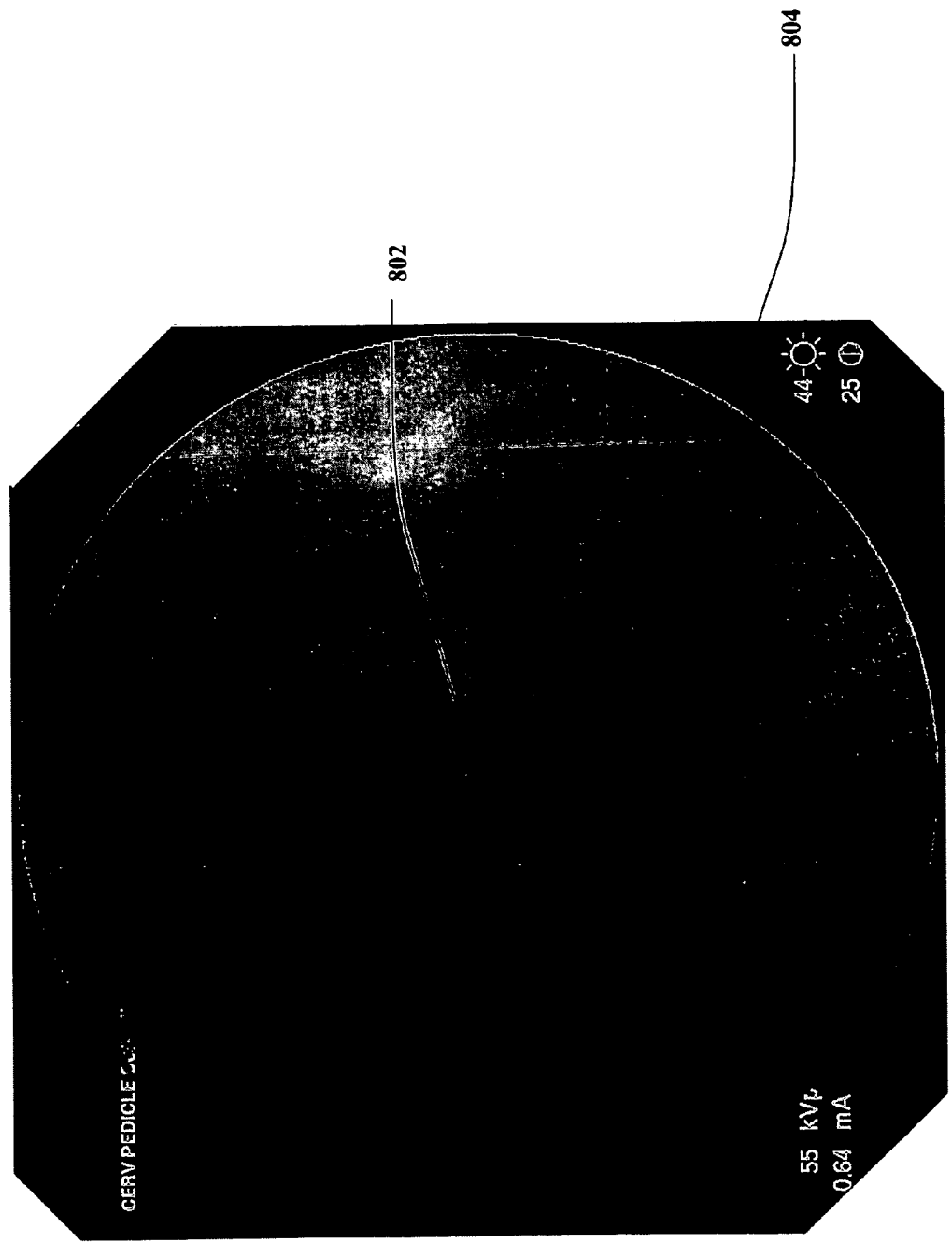
Figure 29:
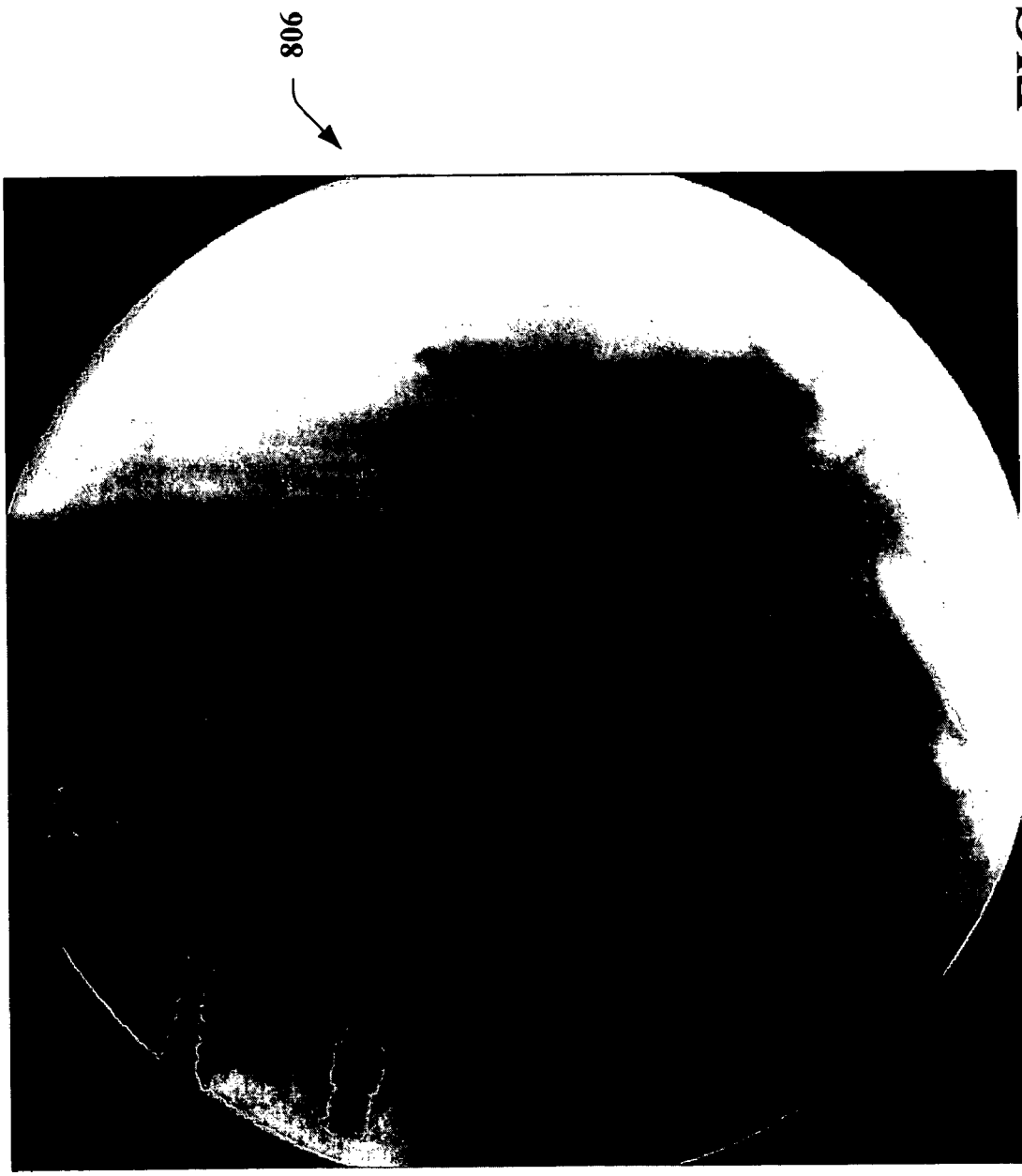

FIGS. 27-44 illustrate methodologies of spinal surgery utilizing intraoperative laser-guided fluoroscopy permitting minimally invasive percutaneous placement of screws and rods and spinal arthrodesis. Referring initially to FIGS. 27-29 illustrated is a methodology for pedicle localization and approach according to an aspect of the invention. A working axis and skin incision point are determined through utilization of laser-guided fluoroscopy along the central axis of the pedicle. The pedicle is the bony process that projects backward from the body of a vertebra, connecting with the lamina on each side and it forms the root of the vertebral arch. The laser 800 should be properly calibrated prior to use to ensure that the crosshairs 802 on the monitor 804 correlate with the path of the laser beam.

The central axis of the pedicle is defined by a line through the center of the entrance, isthmus, and exit of the spinal pedicle. The coaxial fluoroscopic image of the pedicle cortex along its central axis projects as a circle or oval 806 as shown in FIG. 29. The determination of pedicle size and orientation is assessed with preoperative radiographic studies (e.g, x-ray, xeroradiography (XR), computed axial tomography scan (CAT scan), magnetic resonance imaging (MRI), . . . ). Once the coaxial center of the pedicle is lined up with the C-arm crosshair 802, the projection of the laser determines the site of the percutaneous skin incision.

Following prepping and draping of the surgical field in the standard sterile fashion, a guide pin is inserted through the skin incision along the axis of the laser beam and a working portal is established with sequentially larger cannulated dilators 102-116, shown in FIG. 1. The tapered ends and sequential progression of the dilators 102-116 minimize soft tissue trauma. The depth of the soft tissues is determined from the ruler measurement on the dilators. The bony entry point on the posterior spine is confirmed with coaxial fluoroscopy.

With reference also to FIGS. 2-6, an appropriately sized hinged cylinder retractor 200 can be placed over the final or largest used dilator, such as dilator 116, to expose the working area and increase a field of vision 210. The working area and field of vision 210 can be increased by expanding the two hemi-cylinders 212 and 214 of the retractor 200. The two halves of the cylinders 212 and 214 can be variably expanded equally at both proximal and distal ends 202 and 204, as shown in FIG. 3, or the two halves 212 and 214 can be expanded, as in FIG. 4, at the distal end 204 with the proximal end hinged 202. For maximum exposure and field of view 210, the two halves 212 and 214 can be expanded by both methods, wherein the proximal ends 202 are hinged and the distal ends 204 expanded and both halves 212 and 214 are expanded equally at both proximal and distal ends 202 and 204, as illustrated in FIG. 5. Additionally, a smaller retractor oriented at a right angle to and placed within the larger retractor can allow for even greater bi-directional field of vision. The retractors can be fitted with an endoscopic camera and a fiber optic light source for direct visualization.

Figure 30:
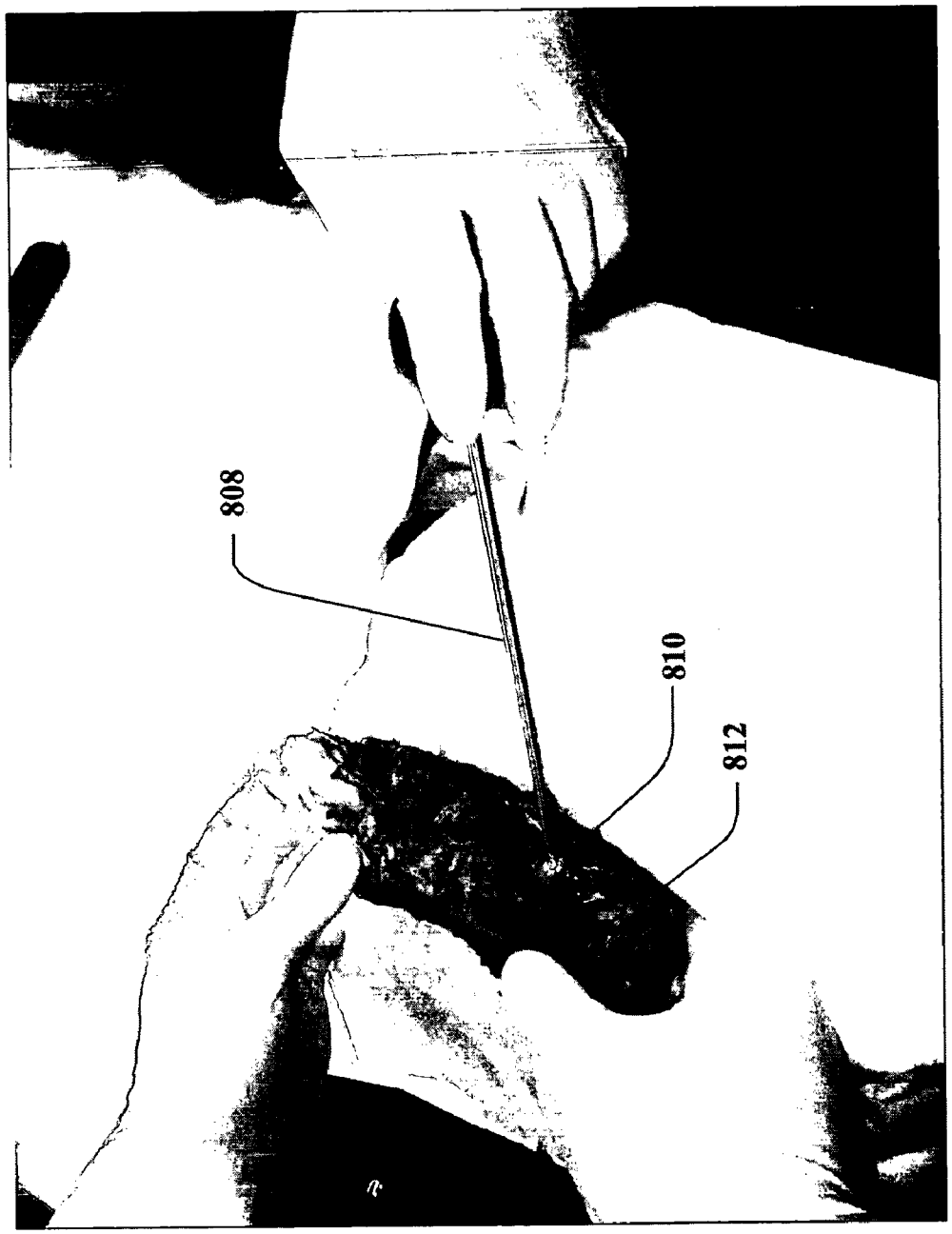
FIGS. 30-40 illustrate a methodology for screw path preparation and placement in accordance with an aspect of the invention.
Figure 31:
Figure 32:
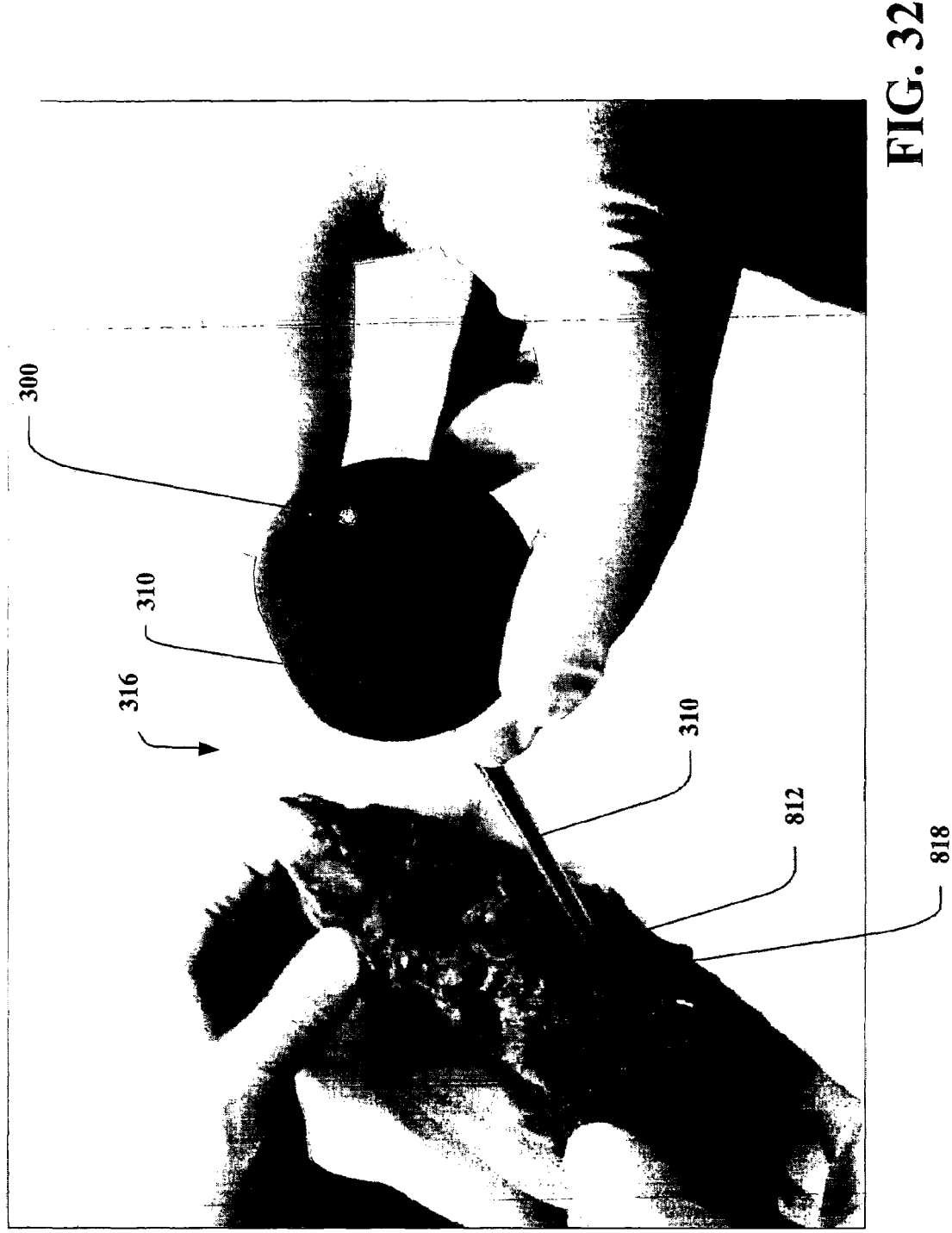

Referring now to FIGS. 30-40 illustrated is a methodology for screw path preparation and placement in accordance with an aspect of the invention. As illustrated in FIG. 30, utilization of a laser-aiming device 808 provides location of the bony entry point 810 on the posterior spine 812, shown removed from a cadaver for illustration purposes only. The proper entry point 810, shown in FIG. 31, is confirmed utilizing coaxial fluoroscopy 814 in accordance with an aspect of the invention. An awl 316 with a radiolucent targeting handle 310 is placed along the working axis utilizing laser-guided fluoroscopy and an entry point 816 is created on the spine 812. The laser-aiming device 300 confirms the proper alignment of all instruments along the working axis utilizing the targeting handle 310. With reference to FIG. 7, the laser-aiming device 300 has a center 302 oriented along the central, longitudinal axis of each instrument.

Figure 33:
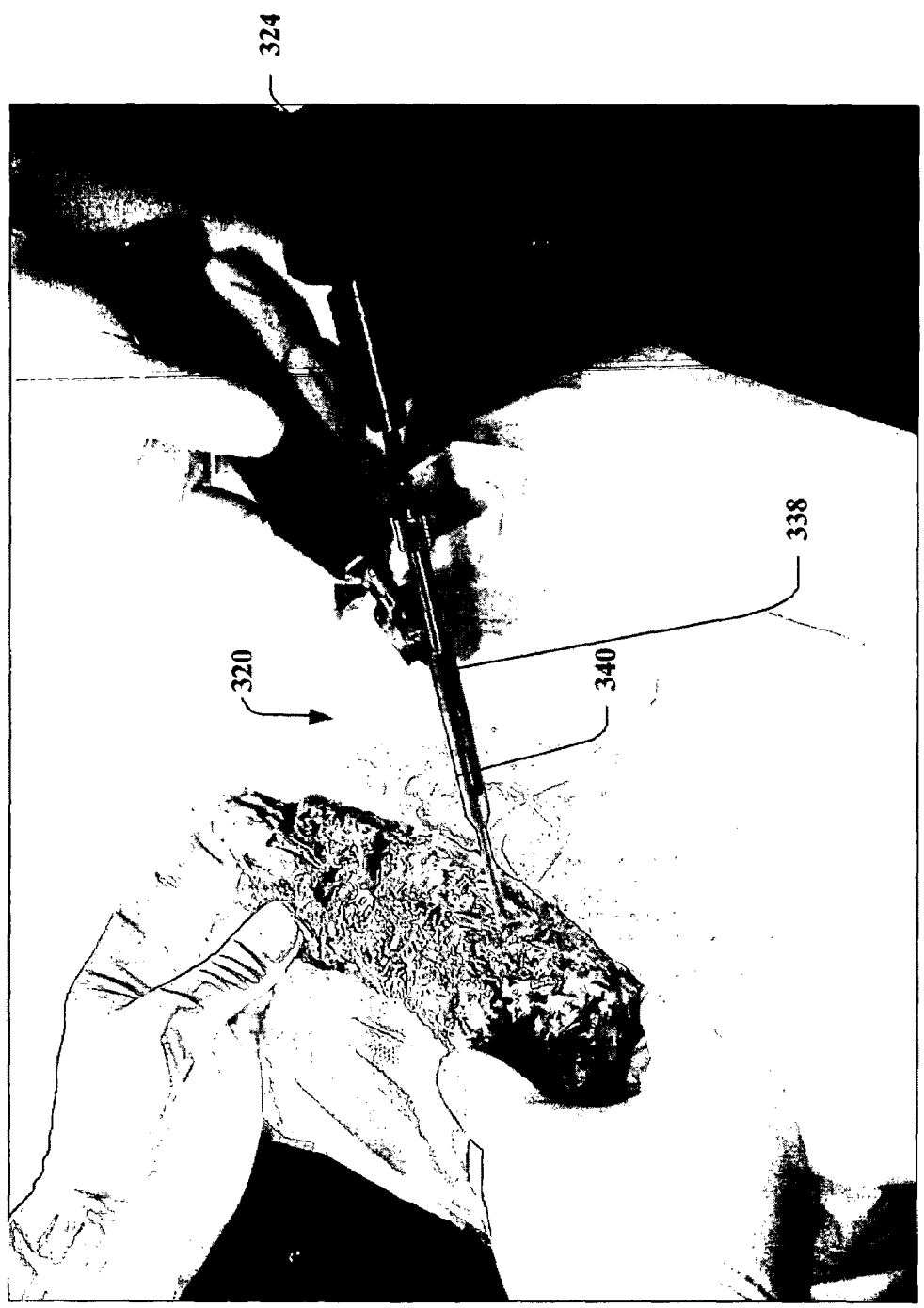
Figure 34:
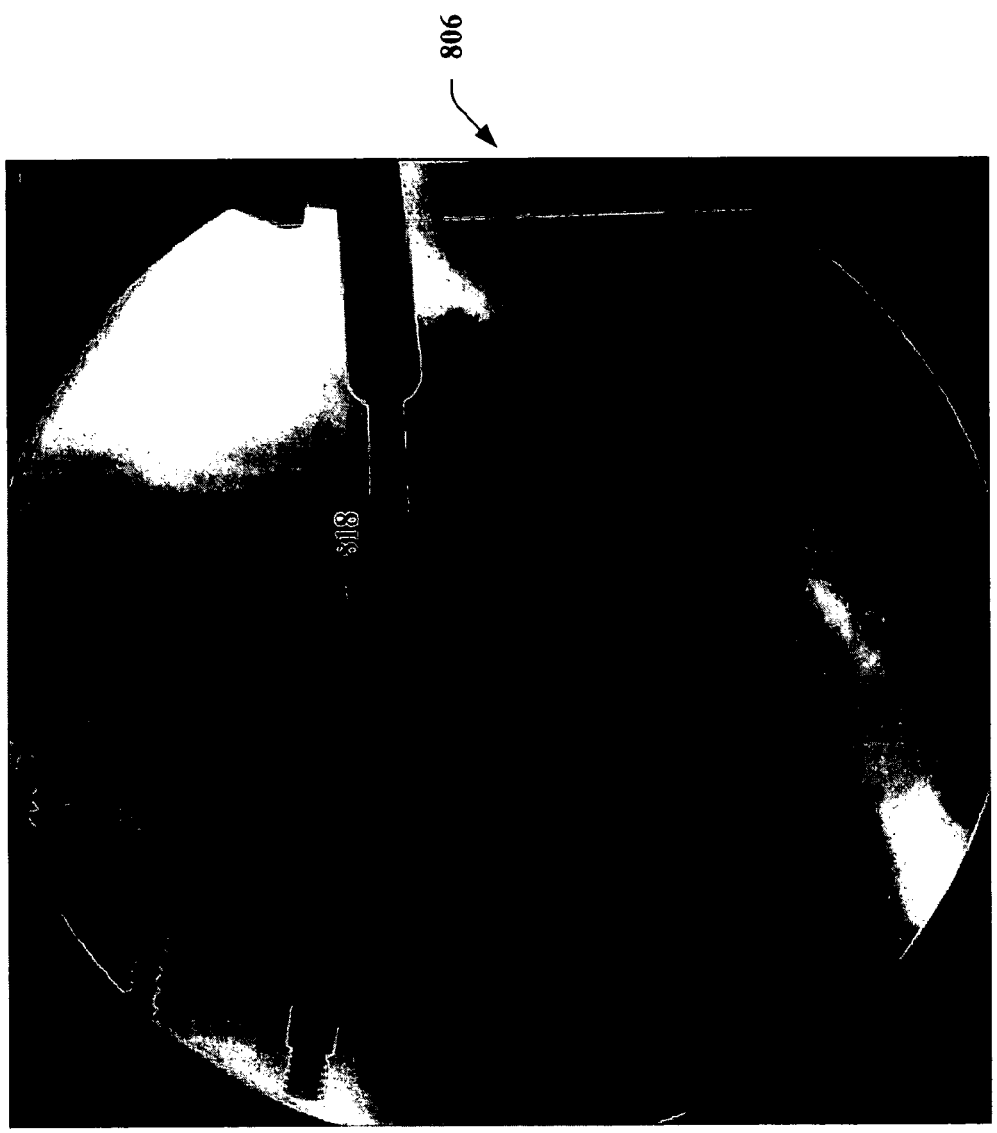
Figure 35:
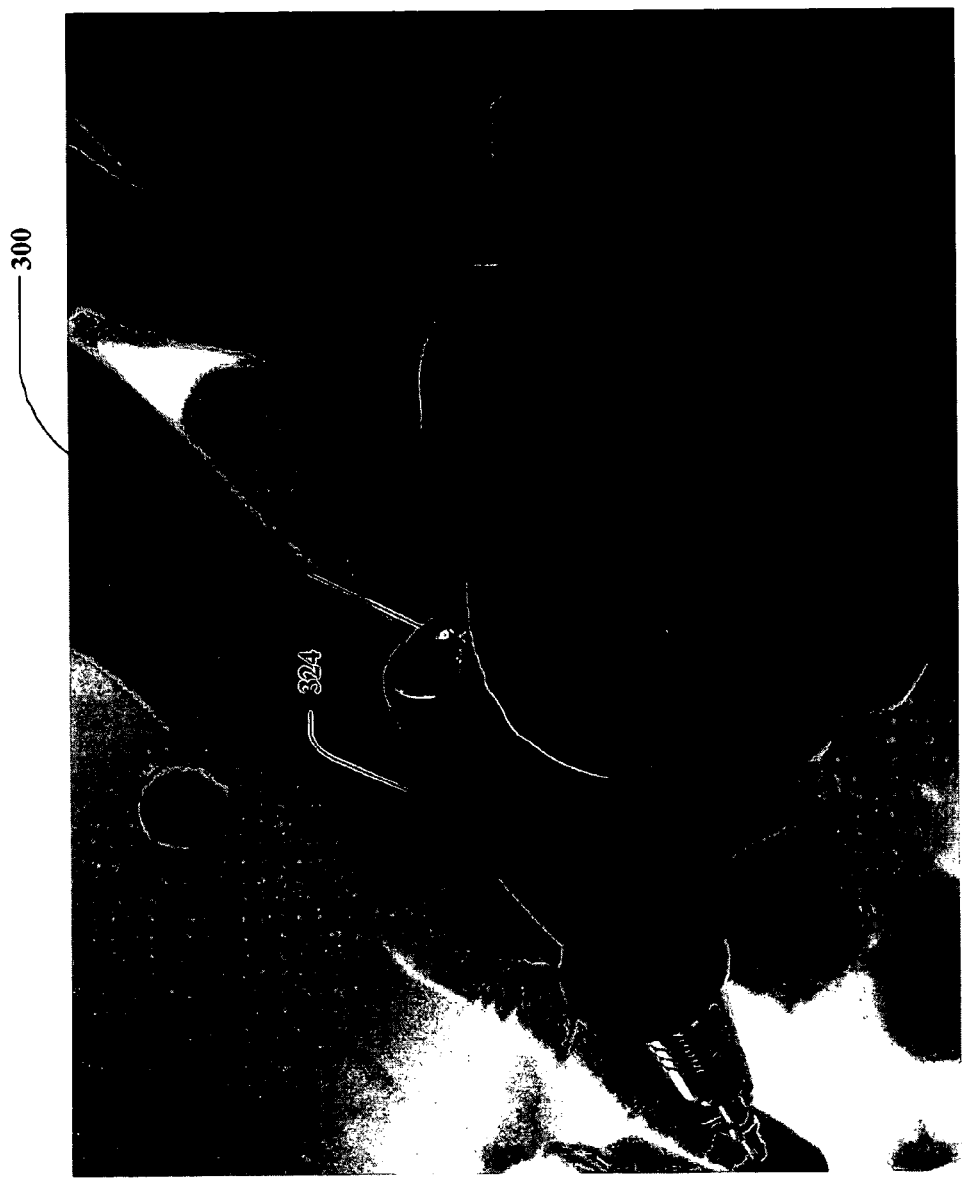
Figure 36:
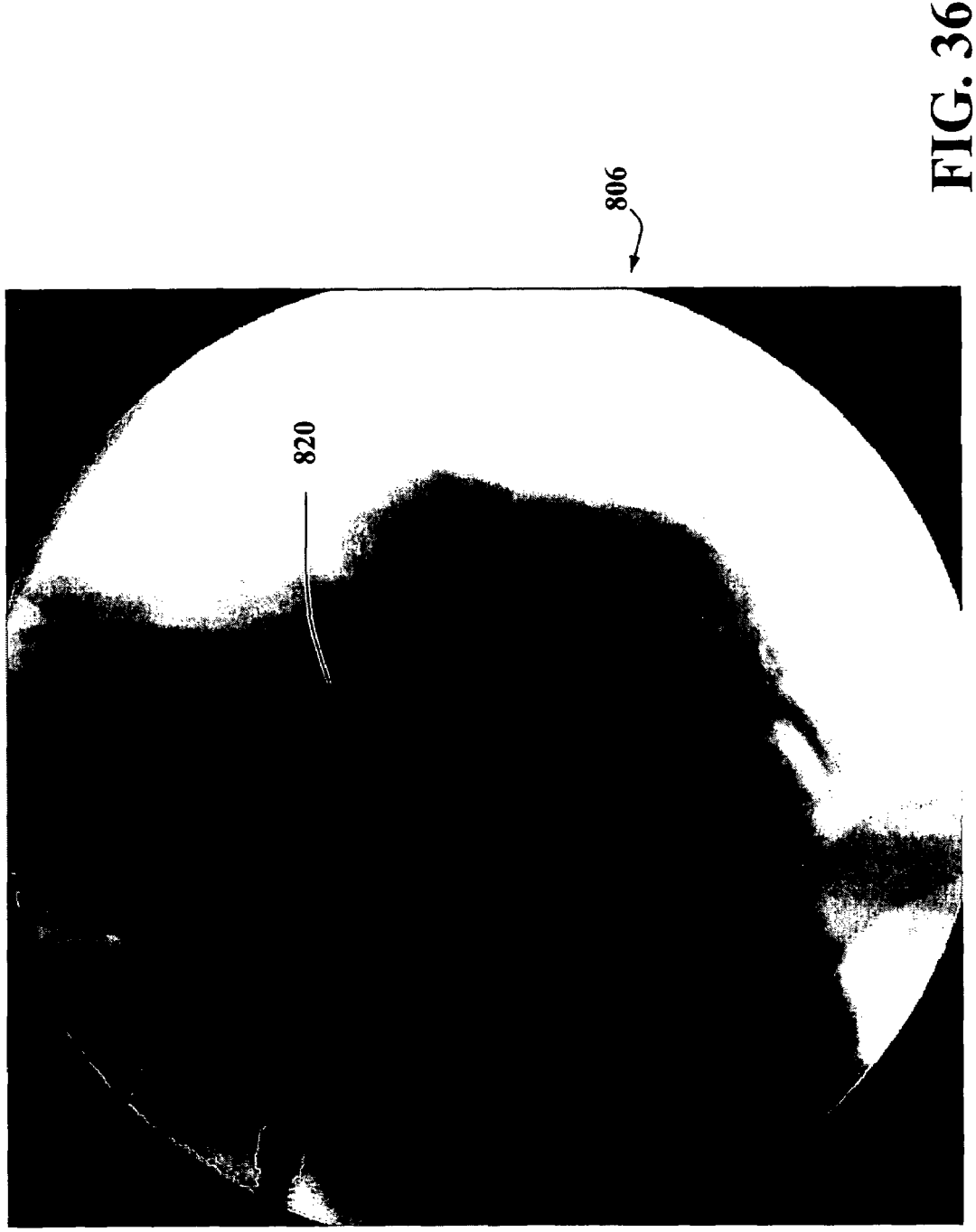
Figure 37:
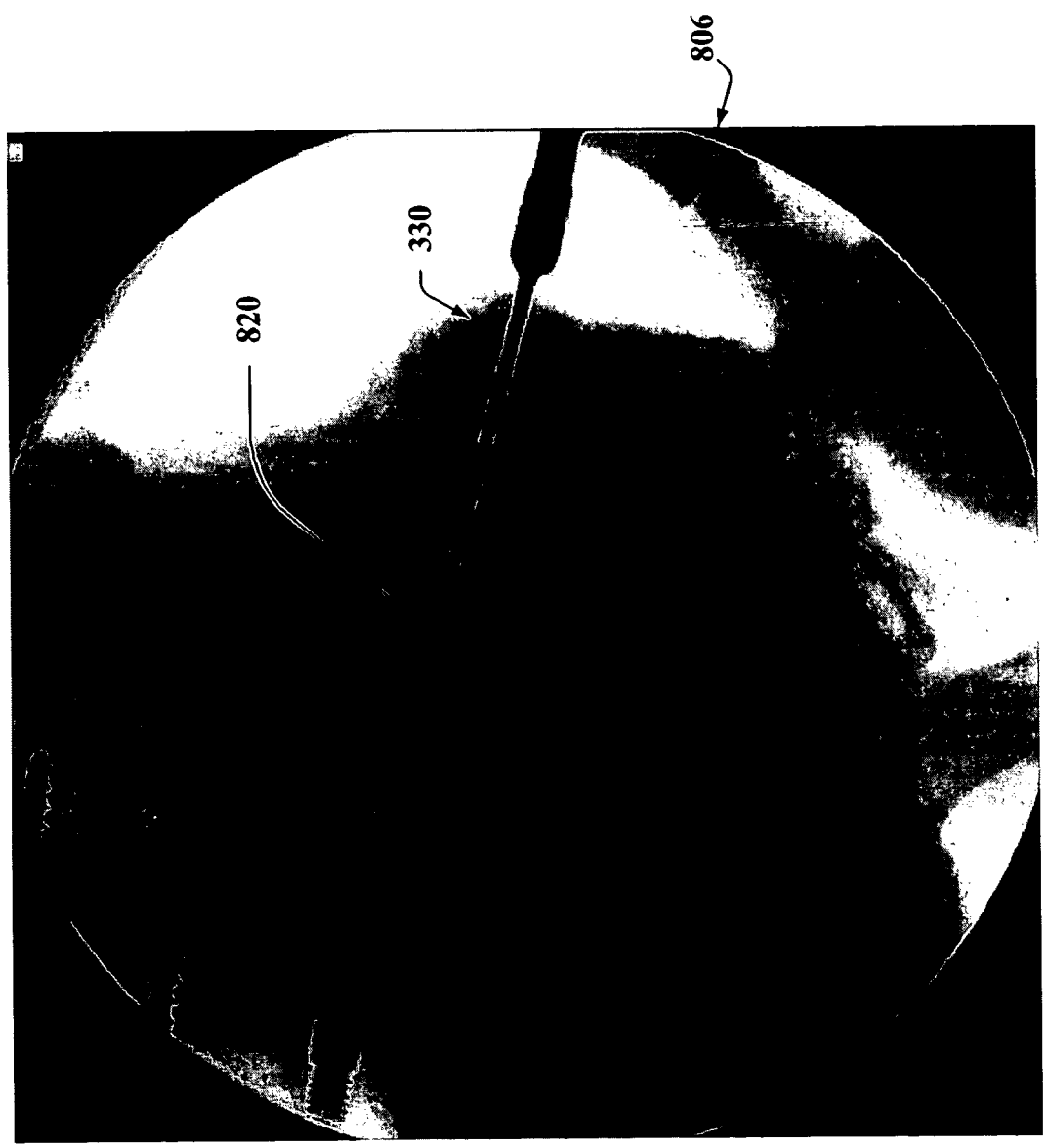

A hand-held drill 320 (or tap) with a radiolucent targeting handle 324 is placed along the working axis as illustrated in FIG. 33. Alternatively, a cannulated drill or tap may be used over a guide pin or wire. The proper entry point 818, shown in FIG. 34, is confirmed utilizing coaxial fluoroscopy according to an aspect of the invention. FIG. 35 illustrates the laser-aiming device 300 shown as a point of light or illuminated area in the handle 324. The laser-aiming device 300 center is oriented along the central, longitudinal axis of each instrument. FIG. 36 illustrates a screw path 820 created along the central axis of the pedicle. The integrity of the pedicle is verified with a ball-tipped probe 330, FIG. 37, with biplanar fluoroscopic images. The coaxial image ensures placement within the pedicle while the lateral image, shown in FIG. 38, of the pedicle verifies drill depth and the rostral-caudal intent of the drill path.

Figure 38:
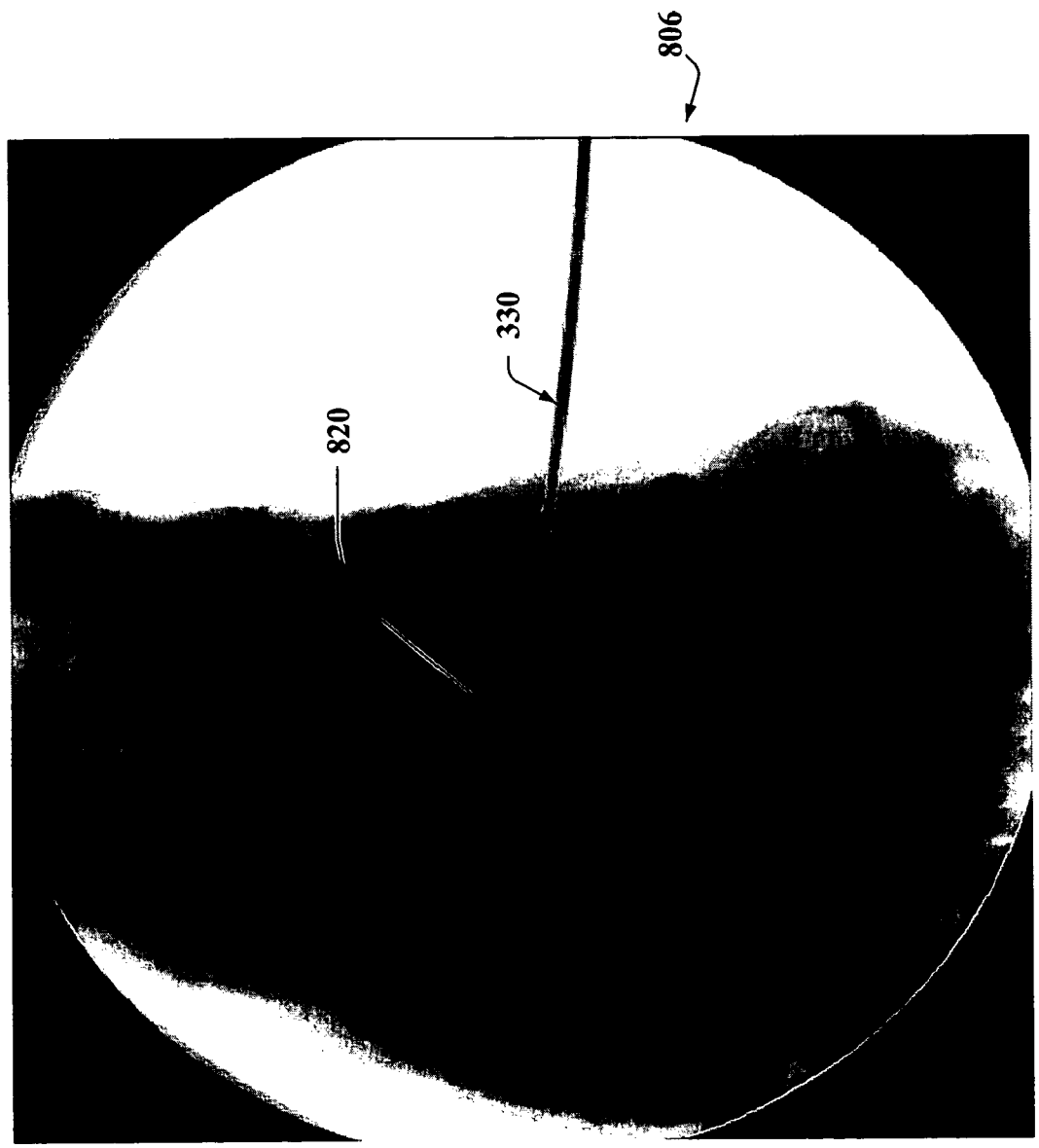
Figure 39:
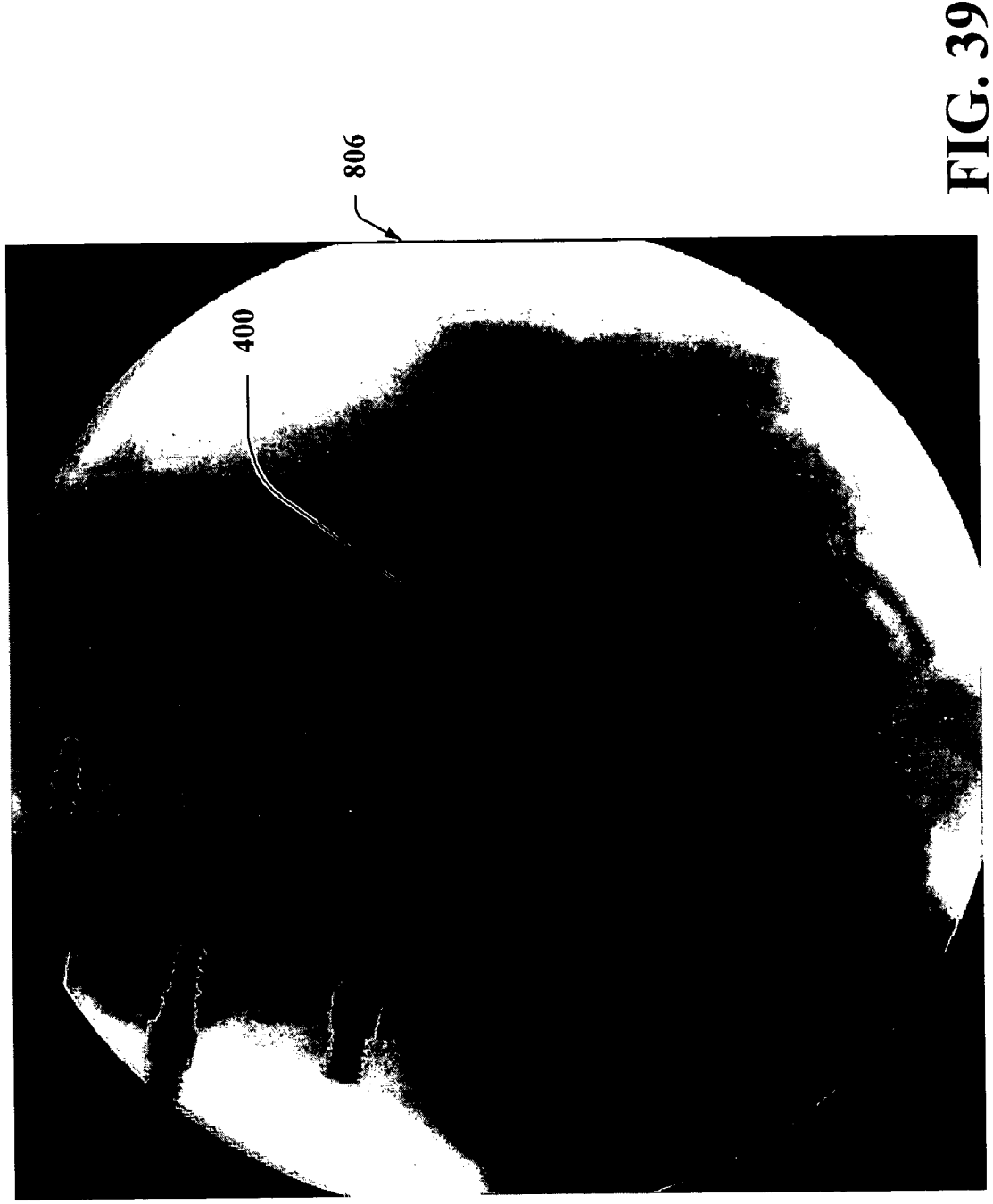
Figure 40:
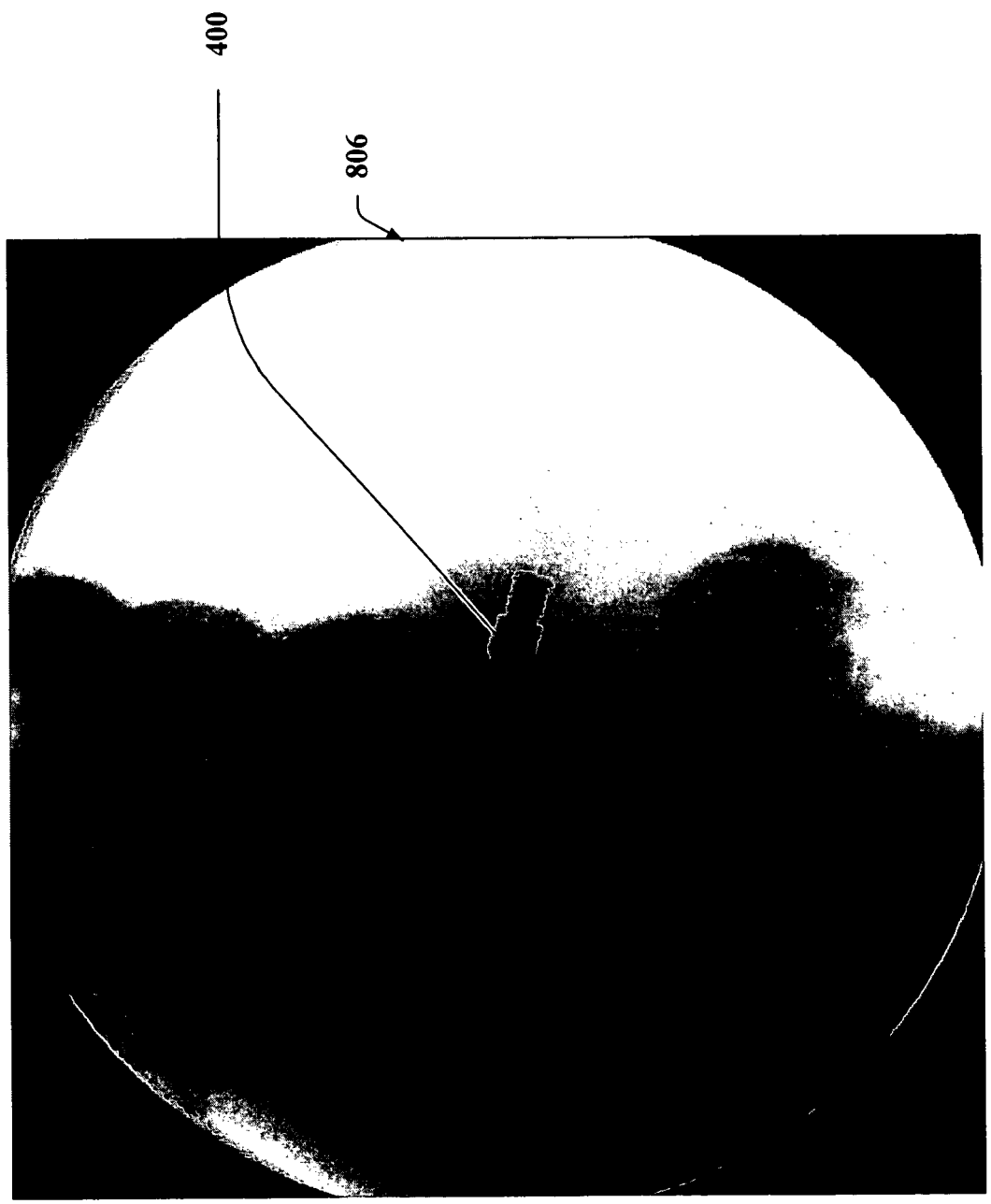
Figure 41:
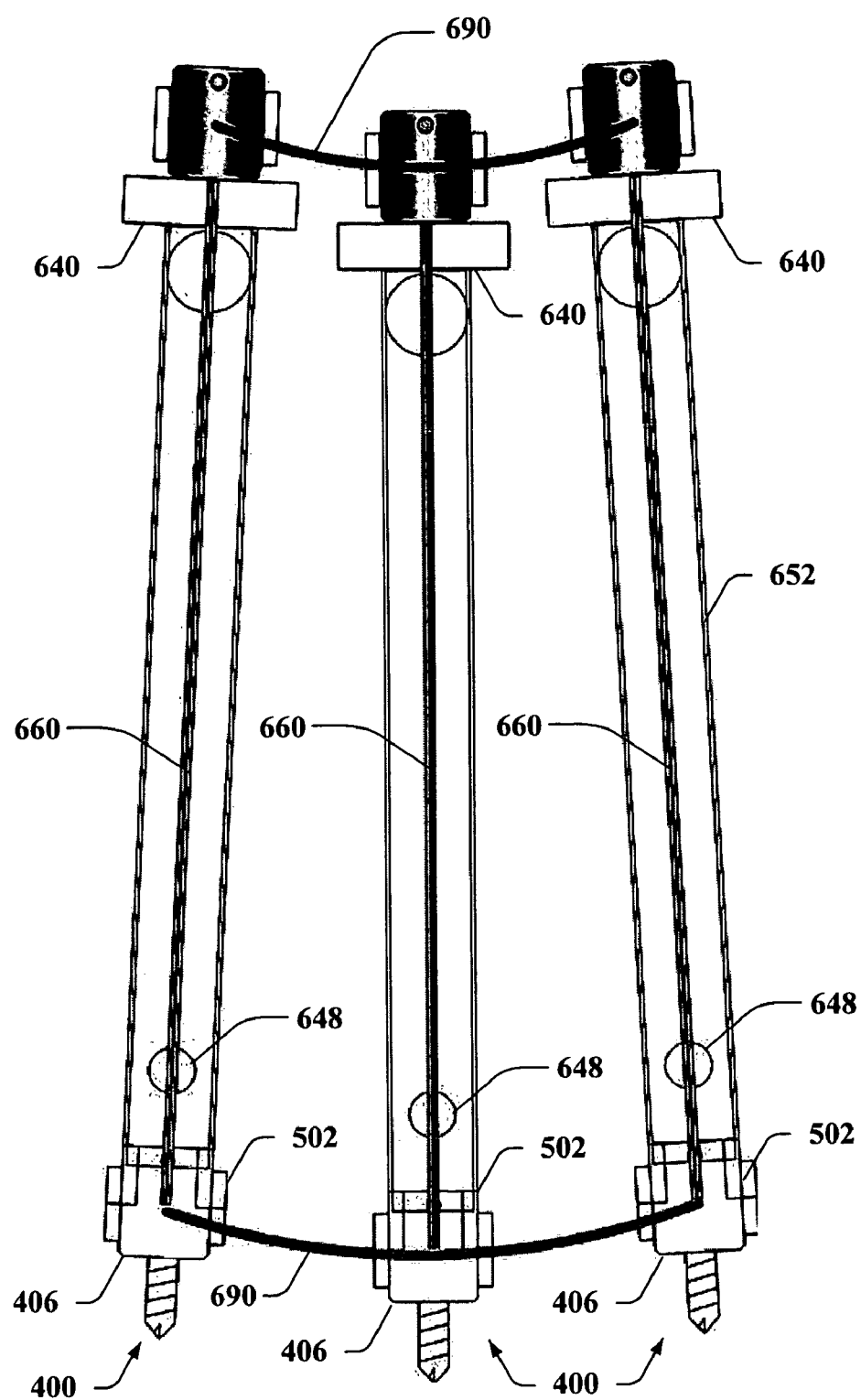
FIGS. 41-44 illustrate a methodology for transconnecting tower placement in accordance with an aspect of the invention.

With reference now to FIGS. 10, 33, and 38 the length of the screw path is measured with a cannulated depth gauge ruler 338 (or from measurement markers on the cannulated drill or tap). A ball-tipped probe 330 is left within the drill path, and the cannulated ruler is placed over the probe, down onto the bone. The measurement is taken from the base of the probe through the open fluted slots 340.

The appropriate length of a screw is chosen based on a depth gauge (or drill/tap) measurement and the diameter of the screw is determined from preoperative radiographic studies (e.g. XR, CT, MRI). Once the proper screw is selected, the polyaxial screw 400 is placed along the drill path with a radiolucent targeting-handled screwdriver 350, shown in FIG. 11. Proper placement of the drill, probe, and screw 400 along the working axis are all confirmed with biplanar fluoroscopy in the coaxial and lateral projections of the central axis of the pedicle, shown in FIGS. 39 and 40. Alternatively, a cannulated polyaxial screw can be placed over an existing guide pin or wire. The above steps are repeated for multi-level pedicle screw instrumentation.

With reference now to FIGS. 41-44 a methodology for transconnecting tower placement in accordance with an aspect of the invention is illustrated. T-handle alignment guides 640 are secured coaxially on the polyaxial screw heads 400 by employing a locking mechanism 502. With reference also to FIGS. 18-24, the locking mechanism(s) 502 is located parallel to the upper T bar(s) 644 and matches with the alignment hole(s) 404 on the closed faces of the polyaxial heads 406. The locking mechanism(s) 502 is composed of two small pegs 512 attached to respective lever arms 514 recessed within the distal tube. The locking mechanism 502 is activated (i.e. pegs are displaced laterally through the alignment holes) when the alignment marker sleeve 650 is placed within the T-handle alignment guide 640. Two round alignment windows 648 are present above both locking mechanisms to facilitate fluoroscopic orientation of the alignment guide during surgery. It will be understood by those skilled in the art that other means of securing the T-handle alignment guide 500 and the screw 400 can be utilized and are within the scope of the invention. For example, a screw mechanism on either side can be utilized wherein matching screws on the distal end of the T-handle alignment guide and the proximal end of the polyaxial screw head are tightened, securing the T-handle alignment guide 500 and the screw 400 together.

The alignment marker sleeves 650 are then placed into the cylindrical chambers 652 of the T-handle alignment guides 640. The cannulated sleeves 650 receive the flexible screw alignment markers 660 and the tip of the sleeves 650 activate the locking mechanisms 502 of the T-handled alignment guides 650.

Figure 42:
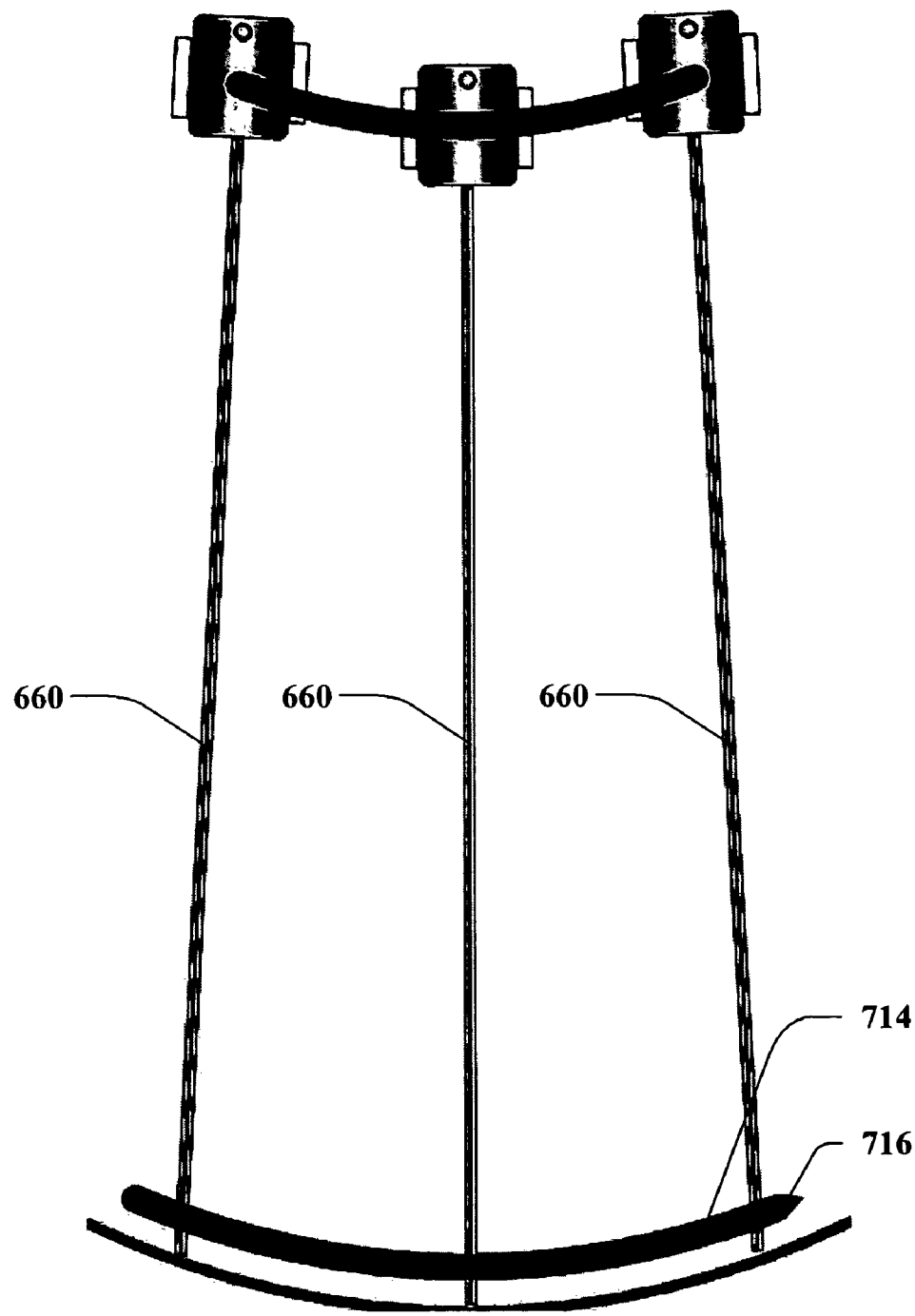
Figure 43:
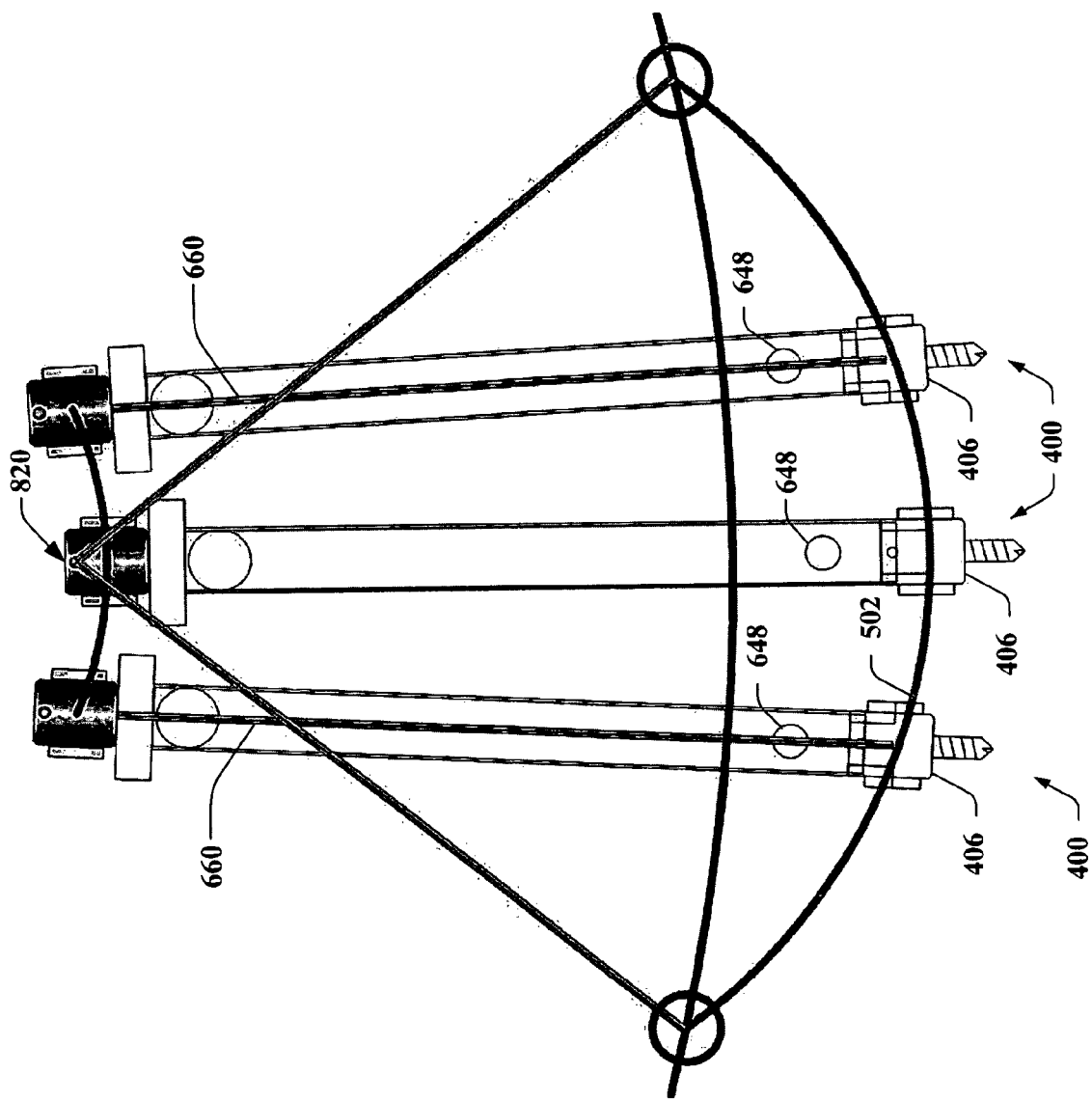
Figure 44:
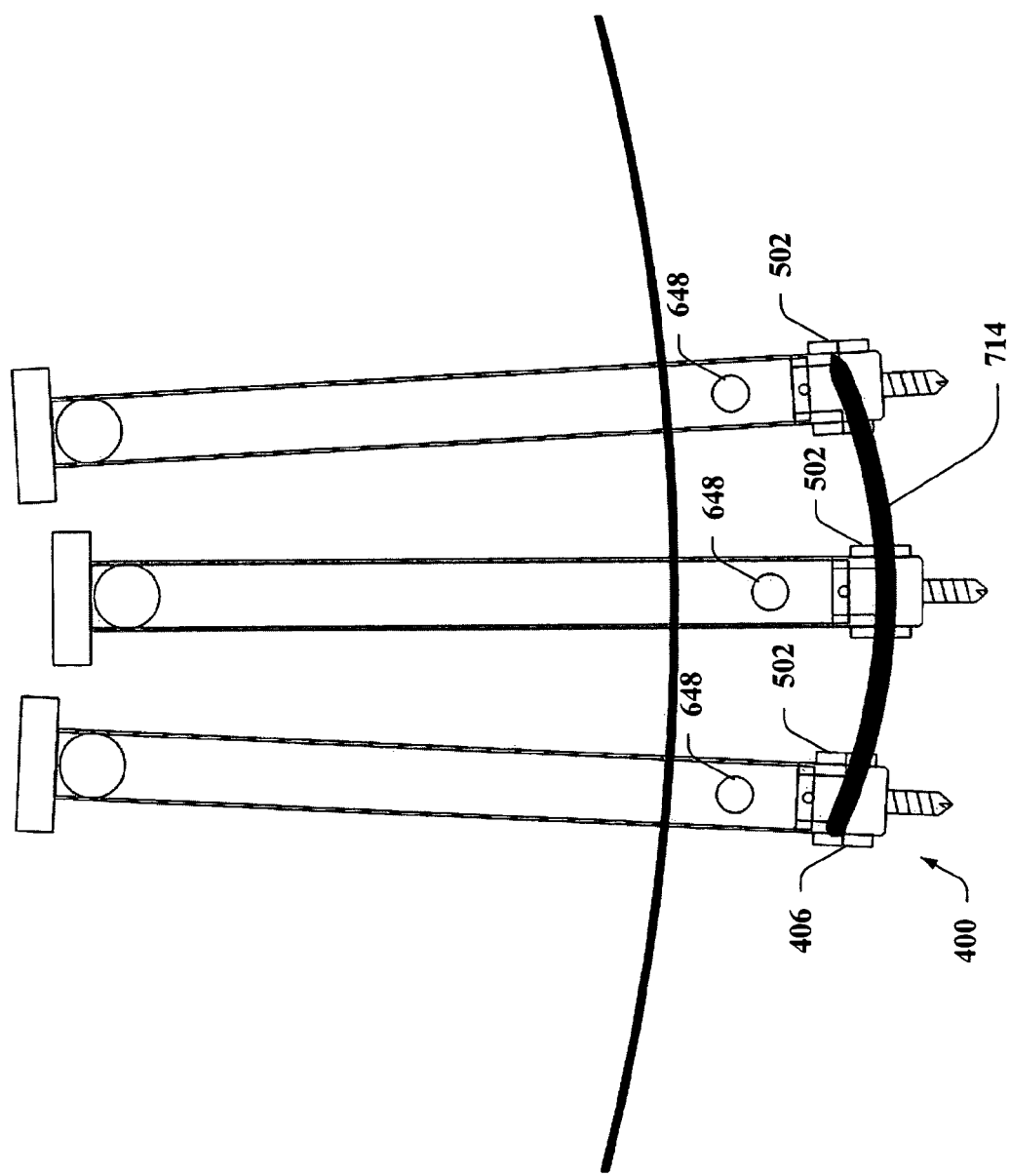

Flexible screw alignment markers 660 are placed within the cannula of the sleeves 650. When the markers 660 are fully seated on the sleeve entry portals, their tips of are located within the centers of the polyaxial screw heads 406. A malleable (or non-malleable) template rod 690 is used to connect a series of flexible alignment markers allowing the alignment markers and connecting template rod can be removed as one unit. A spinal rod 714 with a tapered arrow tip 716 is contoured to match the tips of the screw alignment markers 660 so as to fit through the rod-guidance entry funnels. The shape of the rod 714 should approximate the arc through the polyaxial screw heads 406, as illustrated in FIG. 42 and the length of the rod 714 is measured by the distance between the first and last screw alignment markers 660 and cut to length. The rod 714 is attached to a rod holder 610, as shown in FIG. 17. The rod holder 610 secures the spinal rod 714 at its base end and is employed to guide the leading end of arrow rod through the polyaxial screws 400.

A rod entry skin incision is made along an estimated arc of rotation based on the midpoint 820 of the top of the first and last alignment marker 660. The rod can be placed in either rostral-to-caudal or caudal-to-rostral direction as the direction that affords the greatest ease of insertion should be chosen. The rod is directed through the rod-guidance entry slots of the polyaxial screw heads 400 with bimanual control of the polyaxial screw head 406 with one hand and the spinal rod 714 with the other hand. Guidance can be performed under direct visualization through retractors as well as with biplanar fluoroscopy. The two round alignment windows located at right angles to the rod insertion path can be used to determine intraoperative orientation of the alignment guides, see FIG. 18. The funnel shaped rod-guidance entrance facilitates rod insertion into the open faces of the screws 400. The open faces of the polyaxial screws should be facing each other as the rod is inserted from one rod-guidance entrance to the next. Accurate placement of the spinal rod is confirmed both visually and with fluoroscopic imaging. The rod is finally secured to the screw head 406 with top loading set screws, shown in FIG. 15.

Transconnecting Tower Placement: The placement of connecting towers along the rod path can be determined prior to spinal rod placement. The towers are secured to T-handle alignment guides by employing locking mechanisms, as shown in FIG. 25. The spinal rod is directed through the lower level under direct visualization through retractors and with biplanar fluoroscopy. Alternatively, the lower level of the tower can be open on one side to allow for side loading into an existing spinal rod. The towers should always be positioned between two polyaxial screws. After the lower levels are connected to the spinal rods, the corresponding open faces of the upper level are directed towards each other with the T-handle alignment guides. The length of the connecting rod is assessed with the alignment markers. Following alignment of the open faces along the path of the laser beam, a lateral fluoroscopic image is obtained. The skin incision is determined by the laser's projection onto the skin. The connecting rod is then inserted coaxially along the laser beam path. This is verified with the targeting guide at the base of the rod holder. Controlled guidance of connector rod placement is achieved with biplanar fluoroscopy. When both rods are secured, the entire tower complex is locked with a set screw that seats the connecting rod to the rod locking bolt, and the locking bolt to the spinal rod. Tightening of the set screw seats the rods securely onto their respective saddles, as illustrated in FIG. 26.

Spinal Arthrodesis. This instrumentation technique can be utilized in conjunction with an anterior or posterior spinal fusion. It can be utilized with various anterior interbody fusion procedures performed from the front (e.g. anterior cervical discectomy and fusion, anterior thoracic interbody fusion, anterior lumbar interbody fusion) or from behind (e.g. posterior lumbar interbody fusion, transforaminal lumbar interbody fusion). Posterior or posterolateral spinal fusion can also be performed through direct visualization (i.e. loupe or microscopic magnification) or with endoscopic assistance. Burring and placement of bone graft through the cylinder retractors can be accomplished by employing direct, endoscopic, and/or fluoroscopic visualization. The specialized hinged cylinder retractor can be utilized for arthrodesis procedures. Arthrodesis can be performed prior to, or following percutaneous laser-guided instrumentation.

In another embodiment, this technique can be utilized in the cervical spine to place percutaneous screws and rods into the cervical lateral masses (or pillars) under biplanar, intraoperative laser-guided fluoroscopic imaging. According to another embodiment, the spinal rod insertion steps can be modified by placing a guide wire through the polyaxial heads. An appropriately sized cannulated rod can then be guided over the wire.

It should be noted that any type of spine surgery employed with the subject invention could include spinal fusion. Essentially, spinal fusion is the surgical fusion of two or more vertebrae. During spinal fusion, autogenous bone, allograft bone, bone matrices, or bone-promoting proteins can facilitate the fusion process.

Figure 45:
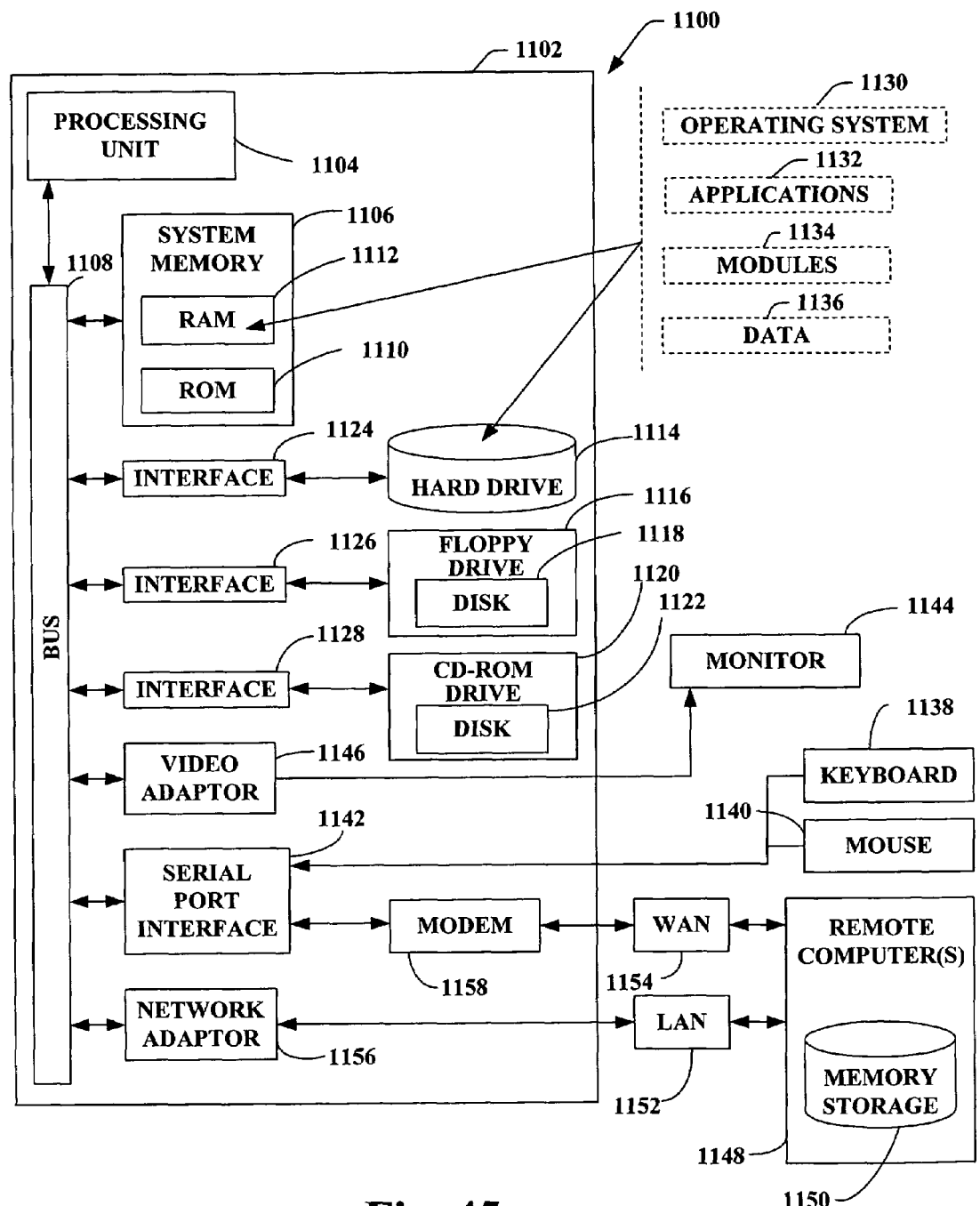
FIG. 45 illustrates a schematic block diagram of an exemplary computing environment in accordance with the invention.

Referring now to FIG. 45, there is illustrated a block diagram of a computer operable to execute the disclosed architecture. In order to provide additional context for various aspects of the invention, FIG. 45 and the following discussion are intended to provide a brief, general description of a suitable computing environment 1100 in which the various aspects of the invention can be implemented. While the invention has been described above in the general context of computer-executable instructions that may run on one or more computers, those skilled in the art will recognize that the invention also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the invention may also be practiced in distributed computing environments where certain tasks are performed by remote processing devices that are linked through a communications network. In a distributed computing environment, program modules can be located in both local and remote memory storage devices. It is to be appreciated that the invention can be implemented with a robot and/or robotic components linked through a communications network.

A computer typically includes a variety of computer-readable media. Computer-readable media can be any available media that can be accessed by the computer and includes both volatile and nonvolatile media, removable and non-removable media. By way of example, and not limitation, computer readable media can comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 45, there is illustrated an exemplary environment 1100 for implementing various aspects of the invention that includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures may also be employed as the processing unit 1104.

The system bus 1108 can be any of several types of bus structure that may further interconnect to a memory bus (with or without a memory controller), a peripheral bus, and a local bus using any of a variety of commercially available bus architectures. The system memory 1106 includes read only memory (ROM) 1110 and random access memory (RAM) 1112. A basic input/output system (BIOS) is stored in a nonvolatile memory 1110 such as ROM, EPROM, EEPROM, which BIOS contains the basic routines that help to transfer information between elements within the computer 1102, such as during start-up. The RAM 1112 can also include a high-speed RAM such as static RAM for caching data.

The computer 1102 further includes an internal hard disk drive (HDD) 1114 (e.g., EIDE, SATA), which internal hard disk drive 1114 may also be configured for external use in a suitable chassis (not shown), a magnetic floppy disk drive (FDD) 1116, (e.g., to read from or write to a removable diskette 1118) and an optical disk drive 1120, (e.g., reading a CD-ROM disk 1122 or, to read from or write to other high capacity optical media such as the DVD). The hard disk drive 1114, magnetic disk drive 1116 and optical disk drive 1120 can be connected to the system bus 1108 by a hard disk drive interface 1124, a magnetic disk drive interface 1126 and an optical drive interface 1128, respectively. The interface 1124 for external drive implementations includes at least one or both of Universal Serial Bus (USB) and IEEE 1394 interface technologies.

The drives and their associated computer-readable media provide nonvolatile storage of data, data structures, computer-executable instructions, and so forth. For the computer 1102, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112.

It is appreciated that the invention can be implemented with various commercially available operating systems or combinations of operating systems.

A user can enter commands and information into the computer 1102 through one or more wired/wireless input devices, e.g., a keyboard 1138 and a pointing device, such as a mouse 1140. Other input devices (not shown) may include a microphone, an IR remote control, a joystick, a game pad, a stylus pen, touch screen, or the like. These and other input devices are often connected to the processing unit 1104 through an input device interface 1142 that is coupled to the system bus 1108, but can be connected by other interfaces, such as a parallel port, an IEEE 1394 serial port, a game port, a USB port, an IR interface, etc.

A monitor 1144 or other type of display device is also connected to the system bus 1108 through an interface, such as a video adapter 1146. In addition to the monitor 1144, a computer typically includes other peripheral output devices (not shown), such as speakers, printers etc.

The computer 1102 may operate in a networked environment using logical connections by wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices, and companies, and facilitate enterprise-wide computer networks, such as intranets, all of which may connect to a global communication network, e.g., the Internet.

When used in a LAN networking environment, the computer 1102 is connected to the local network 1152 through a wired and/or wireless communication network interface or adapter 1156. The adaptor 1156 may facilitate wired or wireless communication to the LAN 1152, which may also include a wireless access point disposed thereon for communicating with the wireless adaptor 1156. When used in a WAN networking environment, the computer 1102 can include a modem 1158, or is connected to a communications server on the LAN, or has other means for establishing communications over the WAN 1154, such as by way of the Internet. The modem 1158, which can be internal or external and a wired or wireless device, is connected to the system bus 1108 by employing the serial port interface 1142. In a networked environment, program modules depicted relative to the computer 1102, or portions thereof, can be stored in the remote memory/storage device 1150. It will be appreciated that the network connections shown are exemplary and other means of establishing a communications link between the computers can be used.

The computer 1102 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with conventional network or simply an ad hoc communication between at least two devices.

Wi-Fi, or Wireless Fidelity, allows connection to the Internet from a couch at home, in a hotel room or a conference room at work, without wires. Wi-Fi is a wireless technology like a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, with an 11 Mbps (802.11b) or 54 Mbps (802.11a) data rate or with products that contain both bands (dual band), so the networks can provide real-world performance similar to the basic 10BaseT wired Ethernet networks used in many offices.

What has been described above includes examples of the subject invention. It is, of course, not possible to describe every conceivable combination of components or methodologies for purposes of describing the invention, but one of ordinary skill in the art may recognize that many further combinations and permutations of the invention are possible. Accordingly, the subject invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates minimally invasive spine surgery, comprising:
   sequential cannulated dilators that create a portal along a working axis;
   a hinged retractor placed over the cannulated dilators that increases a field of vision, the hinged retractor comprising:
   an upper cylinder that has a proximal end and a distal end and a first and second handle operatively connected to the proximal end, the first handle facilitates an angled expansion and the second handle facilitates symmetric expansion;
   a lower cylinder that has a proximal end and a distal end and a handle operatively connected to the proximal end; and
   two hinges operatively connected to the proximal end of the upper cylinder that facilitate expansion of the upper cylinder and the lower cylinder;
   preparation instruments that include a targeted guide with a laser attached to a fluoroscope, the preparation instruments create a path along the working axis;

at least one anchor device;

guidance instruments that selectively insert the at least one anchor device within the spine along the working axis; and a transconnecting tower that has an upper level fitted with alignment holes that include at least one rod-guidance entry funnel and at least one alignment guide hole and a lower level that includes rod-guidance entry funnels, the upper level accommodates a connecting rod and the lower level accommodates a spinal rod.

2. The system of claim 1, the hinged retractor further comprising:

a first position wherein the proximal and distal ends of the upper and lower cylinder are operatively touching;

a second position wherein the upper and lower cylinders are expanded equally at respective proximal and distal ends;

a third position wherein the distal end of the upper cylinder is expanded and the proximal end of the upper cylinder is operatively touching the lower cylinder; and a fourth position wherein the upper and lower cylinders are expanded equally at both the proximal and distal ends and the distal end of the upper cylinder is expanded.

3. The system of claim 1, the preparation instruments comprising: an awl, a hand-held drill or tap, a ball-tipped probe, a depth gauge ruler, and a hexagonal screwdriver.

4. The system of claim 1, the preparation instruments are cannulated to allow for passage over a guide pin or wire.

5. The system of claim 1, the targeting guide is oriented along respective central axes of the preparation system instruments.

6. The system of claim 1, the guidance instruments comprising: a rod with a tapered tip, a T-handle rod holder, a T-handle alignment guide, an alignment marker sleeve, a flexible alignment marker with a polyaxial head, and a template rod.

7. The system of claim 1, the at least one anchor device having a head that accommodates a T-handle alignment guide, the T-handle alignment guide is secured in the head with at least one locking mechanism;

wherein the T-handle alignment guide includes two alignment windows to facilitate fluoroscopic assessment of orientation of the T-handle alignment guide during surgery.

8. The system of claim 6, wherein the alignment marker sleeve is placed within the T-handle alignment guide, and the flexible alignment marker is inserted within a cannula of the alignment marker sleeve.

9. The system of claim 8, further comprising a set screw that seats a connecting rod to a rod locking bolt and the rod locking bolt to the spinal rod.

10. The system of claim 1, the anchor device is a polyaxial screw with a rod guidance funnel face attached to its head.

11. The system of claim 10, the polyaxial screw is cannulated.

12. A method that facilitates minimally invasive spine surgery, comprising:

employing a laser in connection with fluoroscopy to find a working axis;

making an incision in a patient;

inserting a guide pin through the incision along the working axis;

creating a portal with sequential cannulated dilators;

exposing a working area with a hinged cylinder retractor placed over the cannulated dilators;

locating an entry point on the spine with the laser in connection with fluoroscopy;

creating a screw path along the working axis;

placing at least a first polyaxial screw along the screw path;

securing at least a first T-handle alignment guide on the at least a first polyaxial screw;

selectively placing the at least a first polyaxial screw within the spine;

placing at least a first alignment marker sleeve within the first T-handle alignment guide;

inserting at least a first flexible alignment marker within a cannula of the first alignment marker sleeve;

placing at least a second alignment marker sleeve within at least a second T-handle alignment guide, the second T-handle alignment guide secured to at least a second polyaxial screw;

inserting at least a second flexible alignment marker within a cannula of the second alignment marker sleeve; and employing a template rod to connect the first flexible alignment marker with the second flexible alignment marker.

13. The method of claim 12, securing a T-handle alignment guide on the at least a first polyaxial screw further comprising:

placing the at least a first T-handle alignment guide into a head of the at least a first polyaxial screw; and securing the at least a first T-handle alignment guide to the at least a first polyaxial screw.

14. The method of claim 12, the working axis is defined by a targeted guide laser attached to a fluoroscope; the targeted guide laser is oriented along a central axis of a screw preparation instrument.

15. The method of claim 12, further comprising placing at least one transconnecting tower along the screw path between the first and second polyaxial screws, the at least one transconnecting tower having an upper level fitted with alignment holes that include at least one rod-guidance entry funnel and at least one alignment guide hole and a lower level that contain rod-guidance entry funnels.

16. The method of claim 15, further comprising directing a spinal rod through the lower level of the at least one transconnecting tower, and directing a connecting rod through the upper level of the upper level of the transconnecting tower.

17. The method of claim 12, further comprising:

contouring a spinal rod to match the tips of the at least a first alignment marker and the at least a second alignment marker.

18. The method of claim 17, farther comprising:

directing the spinal rod through respective rod-guidance entry funnels of the at least a first polyaxial screw and at least a second polyaxial screw with bimanual control.

19. A system that facilitates minimally invasive spine surgery, comprising:

a plurality of components to be inserted into a spine;

means for employing laser-guided fluoroscopy to selectively place a subset of the plurality of components within the spine;

means for exposing a working area with a hinged cylinder retractor placed over cannulated dilators, the hinged retractor comprising:

an upper cylinder that has a proximal end and a distal end and a first and second handle operatively connected to the proximal end, the first handle facilitates an angled expansion and the second handle facilitates symmetric expansion;

a lower cylinder that has a proximal end and a distal end and a handle operatively connected to the proximal end; and two hinges operatively connected to the proximal end of the upper cylinder that facilitate expansion of the upper cylinder and the lower cylinder; and means for placing connecting towers along a rod path prior to or following spinal rod placement, each connecting tower having an upper level fitted with alignment holes that include at least one rod-guidance entry funnel and at least one alignment guide hole and a lower level that includes rod-guidance entry funnels;

means for directing a connecting rod through the entry funnels of the upper level of the connecting towers; and means for directing a spinal rod through the entry funnels of the lower level of the connecting towers.

* * * * *